(12) United States Patent
Alshaiba Saleh Ghannam Almazrouei et al.

(10) Patent No.: US 11,959,146 B2
(45) Date of Patent: Apr. 16, 2024

(54) INFECTIOUS DISEASE SCREENING DEVICE

(71) Applicant: SHAHEEN INNOVATIONS HOLDING LIMITED, Abu Dhabi (AE)

(72) Inventors: Mohammed Alshaiba Saleh Ghannam Almazrouei, Abu Dhabi (AE); Sajid Bhatti, Abu Dhabi (AE); Jeff Machovec, Abu Dhabi (AE); Clement Lamoureux, Abu Dhabi (AE); Imad Lahoud, Abu Dhabi (AE)

(73) Assignee: Shaheen Innovations Holding Limited, Abu Dhabi (AE)

( * ) Notice: Subject to any disclaimer, the term of this patent is extended or adjusted under 35 U.S.C. 154(b) by 0 days.

(21) Appl. No.: 18/203,584

(22) Filed: May 30, 2023

(65) Prior Publication Data

US 2023/0323483 A1 Oct. 12, 2023

Related U.S. Application Data

(63) Continuation of application No. 17/693,209, filed on Mar. 11, 2022, now Pat. No. 11,667,979, which is a
(Continued)

(30) Foreign Application Priority Data

Jun. 1, 2020 (EP) ..................................... 20177685
Oct. 8, 2020 (EP) ..................................... 20200852
Dec. 15, 2020 (EP) ..................................... 20214228

(51) Int. Cl.
*C12Q 1/70* (2006.01)
*B01L 7/00* (2006.01)
*C12M 1/00* (2006.01)

(52) U.S. Cl.
CPC .................. *C12Q 1/70* (2013.01); *B01L 7/52* (2013.01); *C12M 47/06* (2013.01); *B01L 2300/1805* (2013.01); *B01L 2300/1883* (2013.01)

(58) Field of Classification Search
None
See application file for complete search history.

(56) References Cited

U.S. PATENT DOCUMENTS

| 5,406,503 A | 4/1995 | Williams, Jr. |
| 6,100,084 A | 8/2000 | Miles |

(Continued)

FOREIGN PATENT DOCUMENTS

| CN | 101648041 A | 2/2010 |
| CN | 204070580 U | 1/2015 |

(Continued)

OTHER PUBLICATIONS

European Search Report dated Mar. 6, 2023, 7 pages, for co-pending European Application No. 22207045.0.
(Continued)

*Primary Examiner* — Jyoti Nagpaul
(74) *Attorney, Agent, or Firm* — Amedeo F. Ferraro, Esq.

(57) ABSTRACT

A disease screening device (100) comprising a substrate (101) and a sonication chamber (102) formed on the substrate (101). The sonication chamber (102) is provided with an ultrasonic transducer (105) which generates ultrasonic waves to lyse cells in a sample fluid within the sonication chamber (102). The device (100) comprises a reagent chamber (111) formed on the substrate (101) for receiving a liquid PCR reagent. The device (100) comprises a controller (23) which controls the ultrasonic transducer (105) and a heating arrangement (128) which is provided on the substrate (101). The device (100) further comprises a detection apparatus
(Continued)

which detects the presence of an infectious disease, such as COVID-19 disease.

20 Claims, 23 Drawing Sheets

Related U.S. Application Data continuation of application No. 17/466,906, filed on Sep. 3, 2021, now Pat. No. 11,274,352, which is a continuation of application No. 17/334,531, filed on May 28, 2021, now Pat. No. 11,131,000, which is a continuation-in-part of application No. PCT/GB2021/050822, filed on Apr. 1, 2021.

(60) Provisional application No. 63/064,386, filed on Aug. 11, 2020.

(56) References Cited

U.S. PATENT DOCUMENTS

| | | | |
|---|---|---|---|
| 6,374,684 | B1 | 4/2002 | Dority |
| 6,402,046 | B1 | 6/2002 | Loeser |
| 6,440,725 | B1 | 8/2002 | Pourahmadi |
| 6,601,581 | B1 | 8/2003 | Babaev |
| 6,660,228 | B1 | 12/2003 | Chang |
| 6,679,436 | B1 | 1/2004 | Onishi |
| 6,686,195 | B1 | 2/2004 | Colin |
| 6,878,540 | B2 | 4/2005 | Pourahmadi |
| 6,881,541 | B2 * | 4/2005 | Petersen ............ B01L 3/502 536/25.4 |
| 7,129,619 | B2 | 10/2006 | Yang |
| 7,247,274 | B1 | 7/2007 | Chow |
| 7,279,146 | B2 | 10/2007 | Nassef |
| 8,169,122 | B1 | 5/2012 | Roberts |
| 8,221,700 | B2 | 7/2012 | Steinmiller |
| 8,222,049 | B2 | 7/2012 | Linder |
| 8,591,829 | B2 | 11/2013 | Taylor |
| 8,815,521 | B2 | 8/2014 | Taylor |
| 8,906,624 | B2 | 12/2014 | Seo |
| 8,991,722 | B2 | 3/2015 | Friend |
| 9,052,275 | B2 | 6/2015 | Khattak |
| 9,278,365 | B2 | 3/2016 | Banco |
| 9,415,412 | B2 | 8/2016 | Kawachima |
| 9,580,745 | B2 | 2/2017 | Ermantraut |
| 9,669,409 | B2 | 6/2017 | Dority |
| 9,687,029 | B2 | 6/2017 | Liu |
| 9,687,627 | B2 | 6/2017 | Gallem |
| 9,718,078 | B1 | 8/2017 | Chau |
| 9,867,398 | B2 | 1/2018 | Guo |
| 10,034,495 | B2 | 7/2018 | Alarcon |
| 10,071,391 | B2 | 9/2018 | Yu |
| 10,195,368 | B2 | 2/2019 | Wang |
| 10,300,225 | B2 | 5/2019 | Terry |
| 10,328,218 | B2 | 6/2019 | Reed |
| 10,378,045 | B2 | 8/2019 | Connolly |
| 10,561,803 | B2 | 2/2020 | Liu |
| 10,562,030 | B2 | 2/2020 | Dority |
| 2002/0081669 | A1 | 6/2002 | Festoc |
| 2002/0129813 | A1 | 9/2002 | Litherland |
| 2004/0042936 | A1 | 3/2004 | Ido |
| 2004/0099218 | A1 | 5/2004 | Yang |
| 2004/0200909 | A1 | 10/2004 | McMillan |
| 2004/0224325 | A1 | 11/2004 | Knapp |
| 2005/0244837 | A1 | 11/2005 | McMillan |
| 2006/0030796 | A1 | 2/2006 | Xu |
| 2006/0158956 | A1 | 7/2006 | Laugharn, Jr. |
| 2008/0088202 | A1 | 4/2008 | Duru |
| 2008/0156320 | A1 | 7/2008 | Low |
| 2008/0164339 | A1 | 7/2008 | Duru |
| 2010/0159582 | A1 | 6/2010 | Ismail |
| 2011/0063943 | A1 | 3/2011 | Chow |
| 2012/0009667 | A1 | 1/2012 | Peterson |
| 2014/0087359 | A1 | 3/2014 | Njoroge |
| 2015/0231347 | A1 | 8/2015 | Gumaste |
| 2015/0292038 | A1 | 10/2015 | Seo |
| 2016/0001316 | A1 | 1/2016 | Friend |
| 2017/0135411 | A1 | 5/2017 | Cameron |
| 2017/0303594 | A1 | 10/2017 | Cameron |
| 2018/0042306 | A1 | 2/2018 | Atkins |
| 2018/0153217 | A1 | 6/2018 | Liu |
| 2018/0207551 | A1 | 7/2018 | Lipkens |
| 2018/0029677 | A1 | 10/2018 | Terry |
| 2018/0310625 | A1 | 11/2018 | Alarcon |
| 2018/0343926 | A1 | 12/2018 | Wensley |
| 2019/0046989 | A1 | 2/2019 | Ririe |
| 2019/0242917 | A1 | 8/2019 | Ogg |
| 2019/0255554 | A1 | 8/2019 | Selby |
| 2019/0289918 | A1 | 9/2019 | Hon |
| 2019/0344269 | A1 | 11/2019 | Johnson |
| 2019/0037473 | A1 | 12/2019 | Chen |
| 2019/0381498 | A1 | 12/2019 | Fruchter |
| 2020/0009600 | A1 | 1/2020 | Tan |
| 2020/0016344 | A1 | 1/2020 | Scheck |
| 2021/0024877 | A1 | 1/2021 | Lockhart |

FOREIGN PATENT DOCUMENTS

| | | |
|---|---|---|
| CN | 205432145 U | 8/2016 |
| CN | 205831074 A | 12/2016 |
| CN | 106422005 | 2/2017 |
| CN | 206025223 U | 3/2017 |
| CN | 206079025 U | 4/2017 |
| CN | 106617319 A | 5/2017 |
| CN | 206333372 U | 7/2017 |
| CN | 206586397 U | 10/2017 |
| CN | 206949536 U | 2/2018 |
| CN | 108283331 A | 7/2018 |
| CN | 105747277 B | 8/2018 |
| CN | 105876873 B | 12/2018 |
| CN | 106108118 B | 4/2019 |
| CN | 208837110 U | 5/2019 |
| CN | 110150760 A | 8/2019 |
| CN | 209255084 U | 8/2019 |
| CN | 105876870 B | 11/2019 |
| CN | 209900345 U | 1/2020 |
| CN | 110946315 A | 4/2020 |
| DE | 2656370 C3 | 7/1979 |
| DE | 10122065 A1 | 12/2002 |
| EP | 0353365 A2 | 2/1990 |
| EP | 0 258 637 B1 | 6/1990 |
| EP | 0 442 510 B1 | 1/1995 |
| EP | 0 516 565 B1 | 4/1996 |
| EP | 0 833 695 A1 | 4/1998 |
| EP | 1083952 A2 | 3/2001 |
| EP | 1179585 A2 | 2/2002 |
| EP | 1 618 803 B1 | 12/2008 |
| EP | 3 298 912 A1 | 3/2018 |
| EP | 3 088 007 B1 | 11/2018 |
| EP | 3 434 118 A1 | 1/2019 |
| EP | 3 278 678 B1 | 10/2019 |
| EP | 3 545 778 A1 | 10/2019 |
| FR | 3043576 A1 | 5/2017 |
| FR | 3064502 A1 | 10/2018 |
| GB | 2 403 729 A | 1/2005 |
| GB | 2566766 A | 3/2019 |
| JP | 05093575 U | 12/1993 |
| JP | 2579614 Y2 | 8/1998 |
| JP | 2001069963 A | 3/2001 |
| JP | 2005288400 A | 10/2005 |
| JP | 2008-104966 A | 5/2008 |
| WO | WO 92/21332 A1 | 12/1992 |
| WO | WO9309881 | 5/1993 |
| WO | WO 2002/055131 A2 | 7/2002 |
| WO | WO 2007/083088 A1 | 7/2007 |
| WO | WO 2008/076717 A1 | 6/2008 |
| WO | WO 2009/096346 A1 | 8/2009 |
| WO | WO 2012/062600 A1 | 5/2012 |
| WO | WO 2013/028934 A1 | 2/2013 |
| WO | WO 2014/052671 A1 | 4/2014 |
| WO | WO 2014/113543 A1 | 7/2014 |
| WO | WO 2014/182736 A1 | 11/2014 |
| WO | WO 2015/115006 A1 | 8/2015 |

(56) References Cited

FOREIGN PATENT DOCUMENTS

| WO | WO 2016/118941 A1 | 7/2016 |
|---|---|---|
| WO | WO 2016/196915 A1 | 12/2016 |
| WO | WO 2017/076590 A1 | 5/2017 |
| WO | WO 2017/079636 A1 | 5/2017 |
| WO | WO 2017/143515 A1 | 8/2017 |
| WO | WO 2017/177159 A3 | 10/2017 |
| WO | WO 2017/206022 A1 | 12/2017 |
| WO | WO 2018/041106 A1 | 3/2018 |
| WO | WO 2018/211252 A1 | 11/2018 |
| WO | WO 2018/220586 A2 | 12/2018 |
| WO | WO 2019/048749 A1 | 3/2019 |
| WO | WO 2019/130107 | 7/2019 |
| WO | WO 2019/138076 A1 | 7/2019 |
| WO | WO 2020/019030 A1 | 1/2020 |

OTHER PUBLICATIONS

International Search Report and Written Opinion dated Oct. 13, 2021 for International Appl. No. PCT/GB2021/050822.
International Search Report and Written PCT/GB2021/051332.
International Search Report and Written Opinion dated Sep. 20, 2021 for International Appl. No. PCT/GB2021/051333.
Marentis T.C. et al: "Microfluidic Sonicator for Real-Time Disruption of Eukaryotic Cells and Bacterial Spores for DNA Analysis", Ultrasound in Medicine Biology, New York, NY, US, vol. 31, No. 9, Sep. 1, 2005, pp. 1265-1277, XP027605632, ISSN: 0301-5629 [retrieved on Sep. 1, 2005], p. 1266-p. 1267.
Warner, C.L. et al.: "A Flow-Through Ultrasonic Lysis Module for the Disruption of Bacterial Spores", Journal of the Association for Laboratory Automation, Elsevier, vol. 14, No. 5, Oct. 1, 2009, pp. 277-284, XP026565091, ISSN: 1535-5535, DOI: 10.1016/J. Jala. 2009.04-007 [retrieved on Sep. 3, 2009] pp. 277, 278, p. 281-p. 283.
USPTO Form 892, Notice of References Cited, dated Jul. 21, 2021 for co-pending U.S. Appl. No. 17/334,531, citing U.S. Pat. No. 6,881,541B2 (Peterson, Kurt E.).
UKIPO Invitation to Pay Additional Fees and, Where Applicable, Protest Fee for corresponding PCT application No. PCT/GB2021/050822, dated Jul. 1, 2021.
Extended European Search Report and Search Opinion for corresponding EP Application No. 20214228.7 dated May 26, 2021.
USPTO Form 892, Notice of References Cited, dated Apr. 30, 2021 for co-pending U.S. Appl. No. 16/889,667, citing NPL "Yuan et al".
International Search Report for corresponding PCT Application No. PCT/GB2020/053219 dated Mar. 31, 2021.
EPO search report for corresponding EPO application No. 20200852.0 dated Mar. 26, 2021.
European Search Report dated Feb. 16, 2021 for corresponding EPO Application No. 20177685.3.
Partial European Search Report for corresponding EPO Application No. 20177685.3 dated Nov. 17, 2020.
Written Opinion dated Nov. 10, 2020 for corresponding International Application No. PCT/IB2019/060812.
International Search Report dated Nov. 10, 2020 for corresponding International Application No. PCT/IB2019/060812.
EPO Search Report dated Nov. 9, 2020 for corresponding EPO Application No. 19870059.3 (PCT/IB2019/060808).
Written Opinion dated Nov. 4, 2020 for corresponding International Application No. PCT/IB2019/060806.
International Search Report dated Nov. 4, 2020 for corresponding International Application No. PCT/IB2019/060806.
Written Opinion dated Nov. 4, 2020 for corresponding International Application No. PCT/IB2019/060807.
International Search Report dated Nov. 4, 2020 for corresponding International Application No. PCT/IB2019/060807.
Written Opinion dated Oct. 20, 2020 for corresponding International Application No. PCT/IB2019/060811.
International Search Report dated Oct. 20, 2020 for corresponding International Application No. PCT/IB2019/060811.
Written Opinion dated Oct. 19, 2020 for corresponding International Application No. PCT/IB2019/060810.
International Search Report dated Oct. 19, 2020 for corresponding International Application No. PCT/IB2019/060810.
EPO Search Report dated Sep. 16, 2020 for corresponding EPO Application No. 20168231.
Extended EPO Search Report dated Sep. 15, 2020 for corresponding EPO Application No. 20168938.7.
Written Opinion dated Jun. 25, 2020 for corresponding International Application No. PCT/IB2019/060808.
International Search Report dated Jun. 25, 2020 for corresponding International Application No. PCT/IB2019/060808.
Written Opinion dated Apr. 29, 2020 for corresponding International Application No. PCT/IB2019/055192.
International Search Report dated Apr. 29, 2020 for corresponding International Application No. PCT/IB2019/055192.
LabMate, Microchip RT-PCR COVID-19 Detection System Announced, avail at https://www.labmate-online.com/news/laboratory-products/3/limex-instruments/microchip-rt-pcr-covid-19-detection-system-announced/52084, published Apr. 25, 2020.
EPO search report dated Sep. 20, 2017 for corresponding EPO Application No. 20168245.7.
Yuan et al., Driving an Inductive Piezoelectric Transducer with Class E Inverter, Sensors and Actuators A: Physical, vol. 261, Jul. 1, 2017, pp. 219-227.
Thomas et al., Thermal gradient continuous-flow PCR: a guide to design, Dec. 2014 Microfluidics and Nanofluidics 17(6): 1039-1051 DOI: 10.1007/s 10404-014-1401-3.
Zhang et al., (A new automatic resonance frequency tracking method for piezoelectric ultrasonic transducers used in thermosonic wire bonding, Nov. 2015 Sensors and Actuators A Physical 235:140-150).
Chen et al., Wirelessly addressable heater array for centrifugal microfluids and *Escherichia coli* sterilization, Annu Int Conf IEEE Eng Med Biol Soc. 2013; 2013:5505-8. doi: 10. 1109/EMBC.2013. 6610796.
Cao et al., Plastic microfluidic chip for continuous-flow polymerase chain reaction: simulations and experiments, doi: 10.1002/biot. 201000100. Epub Nov. 4, 2010.
Li et al., A Continuous-Flow Polymerase Chain Reaction Microchip With Regional Velocity Control, J Microelectromech Syst. Feb. 1, 2006; 15(1 ): 223-236.

\* cited by examiner

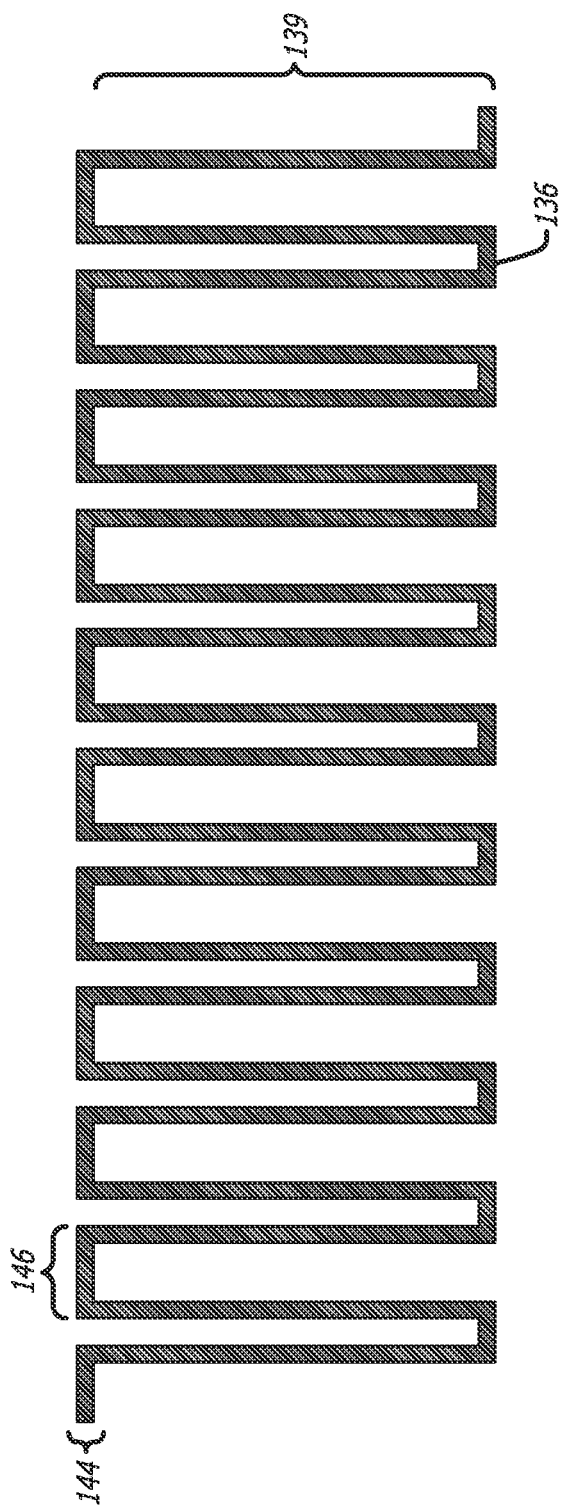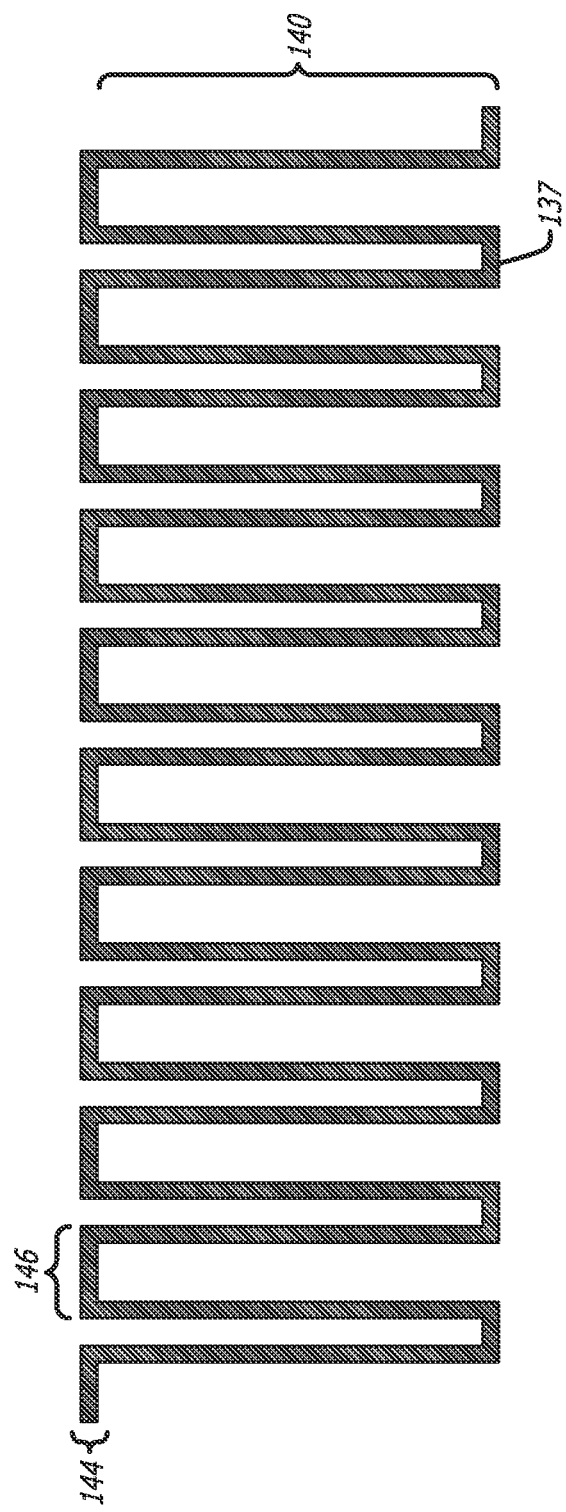
FIG. 34
FIG. 35

INFECTIOUS DISEASE SCREENING DEVICE

CROSS REFERENCE TO RELATED APPLICATIONS

The present application is a continuation of U.S. patent application Ser. No. 17/693,209, filed Mar. 11, 2022, which is a continuation of U.S. patent application Ser. No. 17/466,906, filed Sep. 3, 2021 (now U.S. Pat. No. 11,274,352), which is a continuation of U.S. patent application Ser. No. 17/334,531, ('531 application) filed May 28, 2021 (now U.S. Pat. No. 11,131,000), which is a continuation-in-part of International Patent Application No. PCT/GB2021/050822, filed on Apr. 1, 2021; and the '531 application also claims the benefit of U.S. Provisional Patent Application No. 63/064,386, filed on Aug. 11, 2020, and claims priority to European Patent Application No. 20177685.3, filed on Jun. 1, 2020; European Patent Application No. 20200852.0, filed on Oct. 8, 2020; and European Patent Application No. 20214228.7, filed on Dec. 15, 2020; all of which are incorporated by reference herein in their entirety.

FIELD

The present invention relates to an infectious disease screening device for screening for an infectious disease including, but not limited to, COVID-19 disease. The present invention more particularly relates to a device for screening for viral infections using a Polymerase Chain Reaction (PCR) process including, but not limited to, the screening for SARS-CoV-2 viral infections.

BACKGROUND

Technological advancements in the medical field have improved the efficiency of diagnostic methods and devices. Testing times have reduced drastically, while ensuring reliable results. There are various testing methods to test for infections of all types. To test for viral infections, PCR (Polymerase Chain Reaction) is proven to be the most reliable method. As with other methods, PCR has evolved to be more time-efficient and cost-effective, while maintaining high standards of reliability. PCR is a technique that uses the two matching strands in DNA to amplify a targeted DNA sequence from just a few samples to billions of copies, which are then analyzed using Gel Electrophoresis, which separates DNA samples according to their size.

Conventional Polymerase Chain Reaction (PCR)

A complete conventional PCR test comprises 3 or 4 steps as described below:
1. Cell Lysis and Nucleic Acid (DNA/RNA) Extraction:

Once a patient sample is collected, either from the nose (nasopharyngeal swab) or the throat (oropharyngeal swab), the sample is mixed with the elution buffer. The eluted solution is then filtered to remove any large particles (hair, skin fragments, etc.). The filtered solution is poured into a lysing chamber.

Cell lysis is then performed to break or rupture the lipid bilayer of the cells in the sample to provide a gateway through which cell's components, including DNA/RNA, are extracted.

Cell lysis is performed either chemically or electromechanically, or a combination of both. The process extracts the components and the solution is filtered to separate the nucleic acids (DNA/RNA) from other cell components. The DNA/RNA is then ready for the next step.

2. Reverse Transcription (RT):

This step is only required if the nucleic acid is RNA and not DNA. The process involves introducing an enzyme, known as reverse transcriptase, to the PCR solution containing the RNA to create a complementary DNA (cDNA) sequence from the RNA at a temperature between 40-50° C., The reverse transcription step would precede any PCR related action since PCR requires DNA or cDNA.

3. Polymerase Chain Reaction (PCR)

The principle of PCR is same regardless of the type of DNA sample. PCR requires five core ingredients to be processed: the DNA sample, primers, DNA nucleotide bases, a polymerase enzyme, and a buffer solution to ensure appropriate conditions for the reaction.

The PCR involves a process of heating and cooling known as thermal cycling. The thermal cycling has three steps: Denaturation, Annealing, and Extension. Denaturation starts with heating the reaction solution to 95° C.-100° C. The high temperature is required for separation of the double-stranded DNA or cDNA into single strands.

Annealing is the binding of primers to the denatured strands of sample DNA or cDNA. This process requires a temperature of 55° C.-62° C. Once the temperature is reached, it initiates the annealing stage in which the primers attach to the single strands.

Once the primers are attached, the temperature is raised to around 72° C. for the polymerase to attach and extend the primers along the length of the single strand to make a new double-stranded DNA.

To achieve optimal results, the thermal cycle is repeated ~20-40 times, depending on the number of base pairs required for the test, and ensuring that the desired temperature is achieved at each stage.

4. Gel Electrophoresis

After PCR has been completed, a method known as electrophoresis can be used to check the quantity and size of the DNA fragments produced. DNA is negatively charged and, to separate it by size, the PCR-processed sample is placed in an agarose gel with a current running through the gel that pulls the negatively charged DNA to the opposite end. Larger pieces of DNA encounter more resistance in the solution and therefore do not move as far as smaller segments over the same period of time.

The distance the DNA fragments travel, when compared to a known sample, gives the result of the test. During solution preparation, before the gel electrophoresis step, a fluorescent dye is added in order to see the bands of DNA and based on their location the length of the DNA is known.

Rapid PCR:

Rapid PCR is performed using shorter thermal cycle times (20-60 seconds per cycle) than conventional PCR to reduce overall test times. Rapid PCR also uses real-time PCR, an automated rapid thermocycling process that incorporates amplification and detection in a single process inside a closed reaction vessel. This process significantly reduces the risk of contamination. Rapid PCR uses Fluorescence spectroscopy for detection simultaneously with the PCR's thermal cycles.

Rapid RT-PCR incorporates another process in the overall test when testing for viruses (RNA). The additional process is the Reverse Transcription used to create cDNA from the RNA prior to the PCR process as described above.

Fluorescence Spectroscopy:

Fluorescence spectroscopy is used as an alternative to Gel Electrophoresis to reduce overall duration of the test, Fluorescence spectroscopy uses light to excite the electrons in molecules of certain compounds and causes them to emit light. That light is detected by a detector for fluorescence measurement which can be used for identification of molecule(s) or changes in the molecule.

A global virus outbreak of the SARS-CoV-2 virus (COVID-19 disease), classed as a pandemic has sky-rocketed the demand for virus test kits. The demand also requires tests to be performed more quickly than conventional tests that typically take 4-8 hours to complete, or even rapid tests that take more than 2 hours to give results.

Conventional virus testing methods are usually performed for large quantities of samples and processed simultaneously. However, the long duration for each step, majorly PCR, increases wait-time for results. The rapid-PCR technique provides some lead time over the conventional PCR by reducing the thermal cycle time, shortening the overall test time to around 1-2 hours. However, even this test time is too long for useful mass rapid screening for infectious diseases, such as COVID-19.

There is a need for improved systems and devices for infectious disease screening which alleviate at least some of the problems outlined herein.

SUMMARY

A COVID-19 disease screening device of some arrangements comprises: a substrate which is at least partly composed of silicon; a sonication chamber formed on the substrate, the sonication chamber having a sample inlet, a sample outlet and an ultrasonic transducer, wherein the ultrasonic transducer generates ultrasonic waves in a frequency range of approximately 2800 kHz to approximately 3200 kHz to lyse cells in a sample fluid within the sonication chamber; a controller comprising: an AC driver which generates an AC drive signal at a predetermined frequency within the frequency range of approximately 2800 kHz to approximately 3200 kHz and outputs the AC drive signal to drive the ultrasonic transducer; an active power monitor which monitors active power used by the ultrasonic transducer when the ultrasonic transducer is driven by the AC drive signal, wherein the active power monitor provides a monitoring signal which is indicative of the active power used by the ultrasonic transducer; a processor which controls the AC driver and receives the monitoring signal from the active power monitor; and a memory storing instructions which, when executed by the processor, cause the processor to:
  A. control the AC driver to output the AC drive signal to the ultrasonic transducer at a predetermined sweep frequency;
  B. calculate the active power being used by the ultrasonic transducer based on the monitoring signal;
  C. control the AC driver to modulate the AC drive signal to maximize the active power being used by the ultrasonic transducer;
  D. store a record in the memory of the maximum active power used by the ultrasonic transducer and the sweep frequency of the AC drive signal;
  E. repeat steps A-D for a predetermined number of iterations with the sweep frequency incrementing with each iteration such that; after the predetermined number of iterations has occurred, the sweep frequency has been incremented from a start sweep frequency to an end sweep frequency;
  F. identify from the records stored in the memory an optimum frequency for the AC drive signal which is the sweep frequency of the AC drive signal at which the maximum active power is used by the ultrasonic transducer; and
  G. control the AC driver to output the AC drive signal to the ultrasonic transducer at the optimum frequency, wherein the device further comprises:
a reagent chamber formed on the substrate, the reagent chamber having an inlet and an outlet; the inlet being coupled with the sample outlet of the sonication chamber to permit at least part of a sample fluid to flow from the sonication chamber to the reagent chamber so that the sample fluid mixes with a liquid PCR reagent in the reagent chamber, wherein the device further comprises: a PCR heating apparatus comprising: a channel formed on the substrate, the channel defining a fluid flow path between a channel inlet and a channel outlet; and a first heating element which is carried by the substrate, wherein the first heating element is controlled by the controller to heat a sample fluid flowing along the channel, and wherein the channel inlet is coupled with the outlet of the reagent chamber to receive at least part of a sample fluid from the reagent chamber, wherein the device further comprises: a SARS-CoV-2 virus detection apparatus which is coupled to the channel outlet, wherein the detection apparatus detects a presence of the SARS-CoV-2 virus that causes COVID-19 disease in a sample fluid flowing out of the channel outlet, wherein the detection apparatus provides an output which is indicative of whether or not the SANS-CoV-2 virus detection apparatus detects the presence of the COVID-19 disease in the sample fluid.

In some arrangements, the active power monitor comprises: a current sensor which senses a drive current of the AC drive signal driving the ultrasonic transducer, wherein the active power monitor provides a monitoring signal which is indicative of the sensed drive current.

In some arrangements, the memory stores instructions which, when executed by the processor, cause the processor to: repeat steps A-D with the sweep frequency being incremented from a start sweep frequency of 2800 kHz to an end sweep frequency of 3200 kHz.

In some arrangements, the memory stores instructions which, when executed by the processor, cause the processor to:
in step G, control the AC driver to output the AC drive signal to the ultrasonic transducer at frequency which is shifted by between 1-10% of the optimum frequency.

In some arrangements, the AC driver modulates the AC drive signal by pulse width modulation to maximize the active power being used by the ultrasonic transducer.

In some arrangements, the memory stores instructions which, when executed by the processor, cause the processor to: control the AC driver to alternately output the AC drive signal to the ultrasonic transducer at the optimum frequency for a first predetermined length of time and to not output the AC drive signal to the ultrasonic transducer for a second predetermined length of time.

In some arrangements, the memory stores instructions which, when executed by the processor, cause the processor to: alternately output the AC drive signal and to not output the AC drive signal according to an operating mode selected from:

| Operating mode | First predetermined length of time (seconds) | Second predetermined length of time (seconds) |
| --- | --- | --- |
| 1 | 4 | 2 |
| 2 | 3 | 2 |
| 3 | 2 | 2 |
| 4 | 1 | 2 |
| 5 | 1 | 1 |
| 6 | 2 | 1 |
| 7 | 3 | 1 |
| 8 | 4 | 1 |
| 9 | 4 | 3 |
| 10 | 3 | 3 |
| 11 | 2 | 3 |
| 12 | 1 | 3 |

In some arrangements, the device further comprises: a filter which is provided between the sonication chamber and the reagent chamber to filter sample fluid flowing from the sonication chamber to the reagent chamber.

In some arrangements, the filter has pores of 0.1 μm to 0.5 μm in diameter.

In some arrangements, the device further comprises: at least one further chamber which is formed on the substrate, the at least one further chamber being coupled for fluid communication with the sonication chamber.

In some arrangements, the device further comprises: a plurality of valves which are controlled by the controller to selectively open and close to permit or restrict the flow of liquids between each further chamber and the sonication chamber.

In some arrangements, a further chamber stores a lysing agent having a formula selected from one of: a first lysis formula consisting of 10 mM Tris, 0.25% Igepal CA-630 and 150 mM NaCl; a second lysis formula consisting of 10 mM Tris-HCl, 10 mM NaCl, 10 mM EDTA and 0.5% Triton-X100; or a third lysis formula consisting of 0.1 M LiCl, 0.1 M Tris-HCl, 1% SDS or 10 mm EDTA.

In some arrangements, the sonication chamber has a volume of 100 μl to 1000 μl.

In some arrangements, the sonication chamber contains a plurality of beads, each bead having a diameter of approximately 100 μm.

In some arrangements, the channel comprises a first channel portion having a first cross-sectional area and a second channel portion having a second cross-sectional area, wherein the second cross-sectional area is greater than the first cross-sectional area.

In some arrangements, the first channel portion has a depth of approximately 60 μm and a width of approximately 200 μm, and the second channel portion has a depth of approximately 60 μm and a width of approximately 400 μm.

In some arrangements, the channel comprises a third channel portion having a third cross-sectional area which the same as the first cross-sectional area.

In some arrangements, the first heating element heats a first portion of the channel and the device further comprises: a second heating element which is carried by the substrate, the second heating element being controlled by the controller to heat a sample fluid flowing along a second portion of the channel.

In some arrangements, the device further comprises: a third heating element which is carried by the substrate, the third heating element being controlled by the controller to heat a sample fluid flowing along a third portion of the channel.

In some arrangements; the channel comprises a plurality of first channel portions and a plurality of second channel portions.

An infectious disease screening device of some arrangements comprises: a substrate which is at least partly composed of silicon; a sonication chamber formed on the substrate, the sonication chamber having a sample inlet, a sample outlet and an ultrasonic transducer, wherein the ultrasonic transducer generates ultrasonic waves in a frequency range of approximately 2800 kHz to approximately 3200 kHz to lyse cells in a sample fluid within the sonication chamber; a controller comprising: an AC driver which generates an AC drive signal at a predetermined frequency within the frequency range of approximately 2800 kHz to approximately 3200 kHz and outputs the AC drive signal to drive the ultrasonic transducer; an active power monitor which monitors active power used by the ultrasonic transducer when the ultrasonic transducer is driven by the AC drive signal, wherein the active power monitor provides a monitoring signal which is indicative of the active power used by the ultrasonic transducer; a processor which controls the AC driver and receives the monitoring signal from the active power monitor; and a memory storing instructions which, when executed by the processor, cause the processor to:

A. control the AC driver to output the AC drive signal to the ultrasonic transducer at a predetermined sweep frequency;

B. calculate the active power being used by the ultrasonic transducer based on the monitoring signal;

C. control the AC driver to modulate the AC drive signal to maximize the active power being used by the ultrasonic transducer;

D. store a record in the memory of the maximum active power used by the ultrasonic transducer and the sweep frequency of the AC drive signal;

E. repeat steps A-D for a predetermined number of iterations with the sweep frequency incrementing with each iteration such that, after the predetermined number of iterations has occurred, the sweep frequency has been incremented from a start sweep frequency to an end sweep frequency;

F. identify from the records stored in the memory an optimum frequency for the AC drive signal which is the sweep frequency of the AC drive signal at which the maximum active power is used by the ultrasonic transducer; and G. control the AC driver to output the AC drive signal to the ultrasonic transducer at the optimum frequency, wherein the device further comprises:

a reagent chamber formed on the substrate, the reagent chamber having an inlet and an outlet, the inlet being coupled with the sample outlet of the sonication chamber to permit at least part of a sample fluid to flow from the sonication chamber to the reagent chamber so that the sample fluid mixes with a liquid PCR reagent in the reagent chamber, wherein the device further comprises: a PCR heating apparatus comprising: a channel formed on the substrate, the channel defining a fluid flow path between a channel inlet and a channel outlet; and a first heating element which is carried by the substrate, wherein the first heating element is controlled by the controller to heat a sample fluid flowing along the channel, and wherein the channel inlet is coupled with the outlet of the reagent chamber to receive at least part of a sample fluid from the reagent chamber, wherein the device further comprises: an infectious disease detection apparatus which is coupled to the channel outlet, wherein the detection apparatus detects a presence of an infectious disease in a sample fluid flowing out of the channel outlet, wherein the detection apparatus provides an output which is indicative of whether or not the detection apparatus detects the presence of an infectious disease in the sample fluid.

BRIEF DESCRIPTION OF THE DRAWINGS

So that the present invention may be more readily understood, embodiments of the present invention will now be described, by way of example, with reference to the accompanying drawings, in which:

FIG. 34 is a schematic top view of a first heating element of the PCR heating arrangement shown in FIG. 31, FIG. 35 is a schematic top view of a second heating element of the PCR heating arrangement shown in FIG. 31.

DETAILED DESCRIPTION

Figure 1:
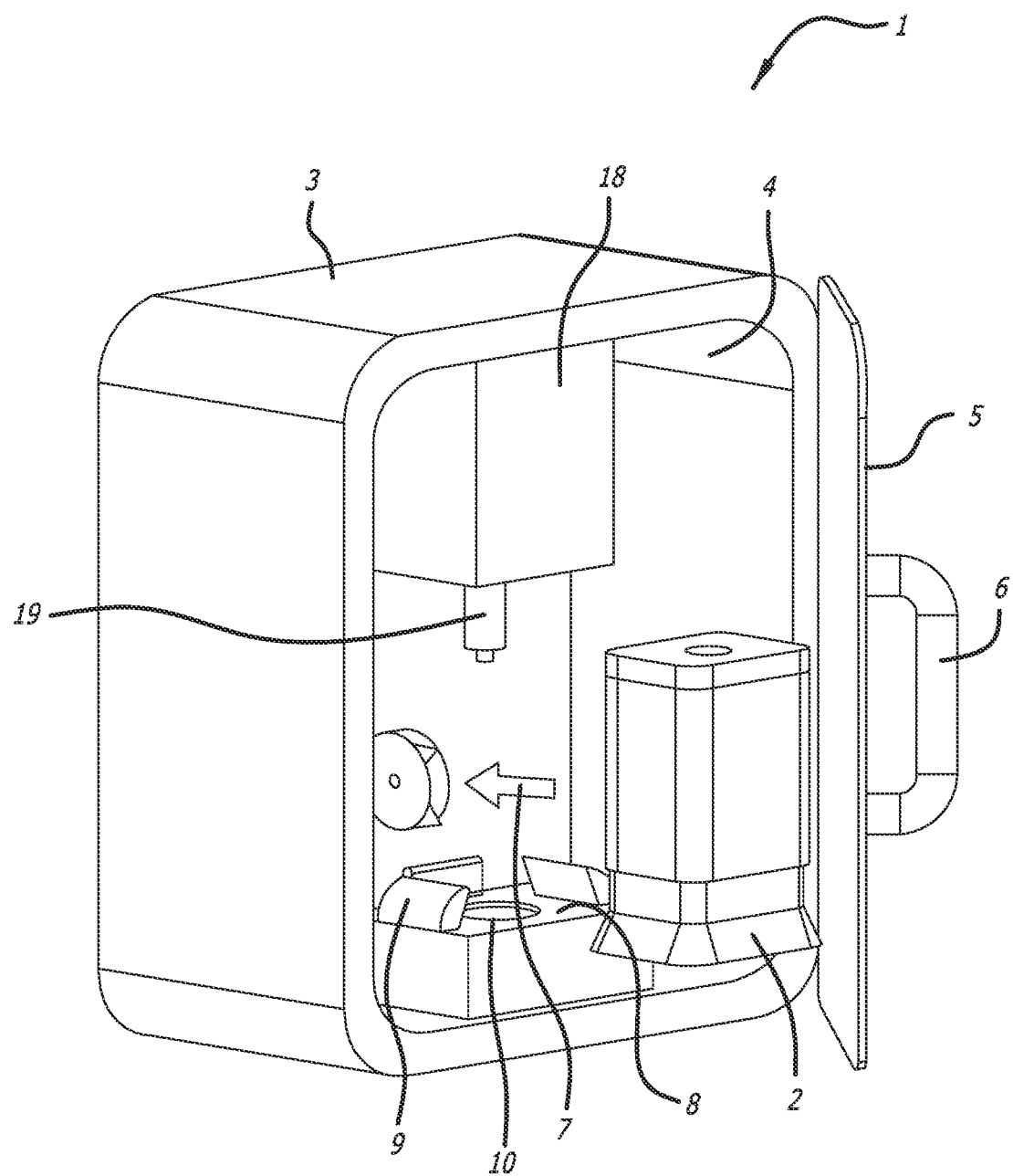
FIG. 1 is a perspective schematic view of a system of some arrangements with an assay device of some arrangements.

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

The following disclosure provides many different embodiments, or examples, for implementing different features of the provided subject matter. Specific examples of components, concentrations, applications and arrangements are described below to simplify the present disclosure. These are, of course, merely examples and are not intended to be limiting. For example, the attachment of a first feature and a second feature in the description that follows may include embodiments in which the first feature and the second feature are attached in direct contact, and may also include embodiments in which additional features may be positioned between the first feature and the second feature, such that the first feature and the second feature may not be in direct contact. In addition, the present disclosure may repeat reference numerals and/or letters in the various examples. This repetition is for the purpose of simplicity and clarity and does not in itself dictate a relationship between the various embodiments and/or configurations discussed.

The following disclosure describes representative arrangements or examples. Each example may be considered to be an embodiment and any reference to an "arrangement" or an "example" may be changed to "embodiment" in the present disclosure.

This disclosure establishes improved aspects of a rapid result diagnostic assay system designed for point of care (POC) and/or home use for infectious disease screening, specifically SARS-CoV-2 known to cause COVID-19 disease.

The assay devices and systems of some arrangements are for screening any other infectious disease caused by pathogens, such as bacteria or viruses. In some arrangements, the assay devices and systems are for screening for an infectious agent or disease selected from a group including, but not limited to, influenza, coronavirus, measles, HIV, hepatitis, meningitis, tuberculosis, Epstein-Barr virus (glandular fever), yellow fever, malaria, norovirus, zika virus infection or anthrax.

In some arrangements, the assay devices and systems are for screening a target sample in the form of a saliva sample, a sputum sample or a blood sample. In other arrangements, the assay devices and systems are for screening a target sample which is collected from a user by a nasopharyngeal swab or an oropharyngeal swab.

The assay system of some arrangements comprises 13 main components: an assay device or pod containing various liquid chambers, a plunger column, a flow directing cog, a sonication chamber, a filtration array, a PCR fin, PCR reagents, a PCR method, a thermal cycler, an infectious disease detection apparatus, a lid, a method for reporting results, and a housing that contains all necessary parts to manipulate the pod.

Referring to FIG. 1 of the accompanying drawings, a system 1 for infectious disease screening is configured for use with a removable assay device 2 which, in this arrangement, is in the form of a single-use pod. In some arrangements, the system 1 is provided separately from the assay device 2. In other arrangements, the system 1 is provided in combination with the assay device 2. In further arrangements, the assay device 2 is provided without the system 1 but for use with the system 1.

The system 1 comprises a housing 3 which houses the various components of the system 1. In this arrangement, the housing 3 comprises an opening 4 which is closed by a door 5. The door 5 is configured to move between an open position, as shown in FIG. 1 and a closed position in which the door 5 closes the opening 4 in the housing 3. In this arrangement, the door 5 is provided with a handle 6 to facilitate opening and closing by a user. In this embodiment, the door 5 is provided to enable a user to open the system 1 to insert the assay device 2 into the system 1, as indicated generally by arrow 7 in FIG. 1. Other arrangements incorporate a different access means to permit a user to insert the assay device 2 into the system 1.

In this arrangement, the system 1 is a portable system. The housing 3 is compact to enable the system 1 to be carried easily and for the system 1 to be positioned unobtrusively at a convenient location, such as adjacent an entrance door of a building. The portable configuration of the system 1 of some arrangements enables the system 1 to be carried easily to a location where there is a need for infectious disease screening. In some arrangements, the system 1 is configured to be powered by a battery or another low power source of electricity so that the system 1 can be used at a remote location, without the need for mains electricity. In other arrangements, the system 1 comprises a power source input to be connected to mains electricity to power the system 1 and/or to charge a battery within the system 1.

The system 1 comprises a support platform 8 which is provided at the base of the housing 3. The support platform 8 comprises a surface for carrying the assay device 2. The support platform 8 comprises a plurality of guide members 9 which are located around the support platform 8 to guide the assay device 2 into a predetermined position when the assay device 2 is inserted into the system 1. In this arrangement, the support platform 8 is provided with a central aperture 10 which is positioned beneath the assay device 2 when the assay device 2 is carried by the support platform 8.

Figure 2:
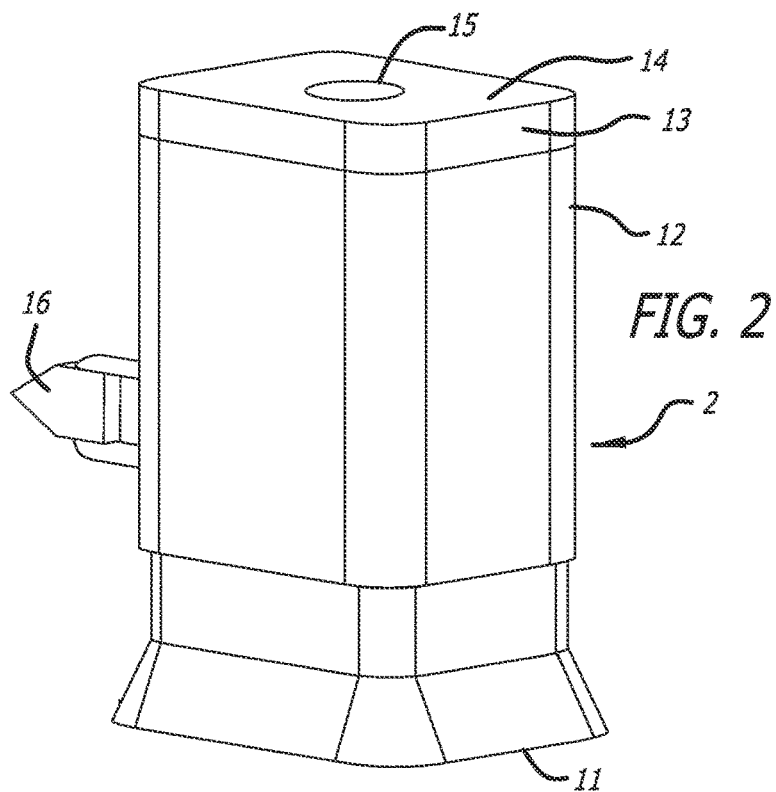
FIG. 2 is a schematic drawing of an assay device of some arrangements.
Figure 3:
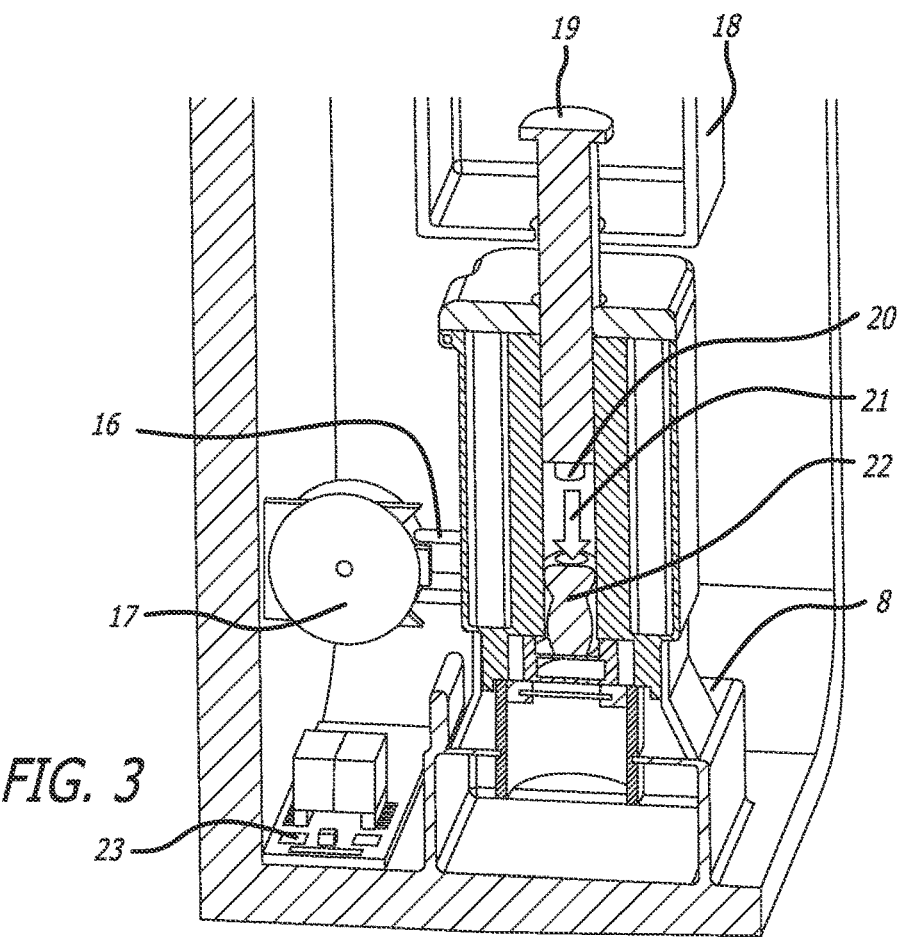
FIG. 3 is a schematic drawing of part of a system of some arrangements with an assay device of some arrangements.

Referring now to FIG. 2 of the accompanying drawings, the assay device 2 comprises a base 11 which, in this arrangement, comprises an enlarged lower end in order to provide stability to the assay device 2 when the assay device 2 is resting on the base 11. The assay device 2 further comprises an assay device housing 12 which houses the internal components of the assay device 2, which are described in more detail below. The assay device housing 12 comprises an upper end 13 which is remote from the base 11 and which is configured to be opened to provide access to within the assay device 2. A cover 14 is movably mounted to the assay device housing 12 to at least partly cover the upper end 13. The cover 14 comprises a central aperture 15. The cover 14 will be described in more detail below.

The assay device 2 comprises a PCR apparatus 16 which protrudes from one side of the assay device 2. The PCR apparatus 16 will be described in more detail below.

Figure 8:
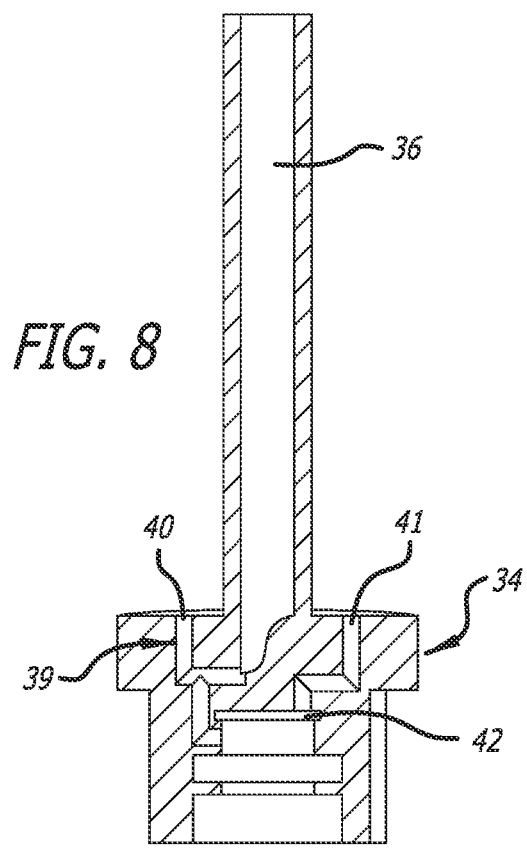
FIG. 8 is a cross-sectional view of the part of the assay device shown in FIG. 7.

Referring now to FIG. 8 of the accompanying drawings, when the assay device 2 is inserted into the system 1, the assay device 2 is guided into the predetermined position on the support platform 8 such that the PCR apparatus 16 is at least partly received within a heating recess of a heating apparatus 17, which is described in detail below.

The assay device 2 sits beneath a drive arrangement 18 which forms part of the system 1. In this arrangement, the drive arrangement 18 comprises a drive element in the form of a plunger 19 which is configured to be moved by the drive arrangement 18 outwardly from the drive arrangement 18 so that a tip 20 of the plunger 19 moves through the aperture 15 in the cover 14 of the assay device 2 along the direction generally indicated by arrow 21 to engage a piston 22 within the assay device 2. The system 1 is configured to extend and retract the plunger 19 in order to move the piston 22 during the operation of the system 1.

The system 1 comprises a controller 23 which incorporates a computing device, such as a microprocessor, and a memory. The controller 23 is configured to control the operation of the system 1 as described below.

Figure 4:
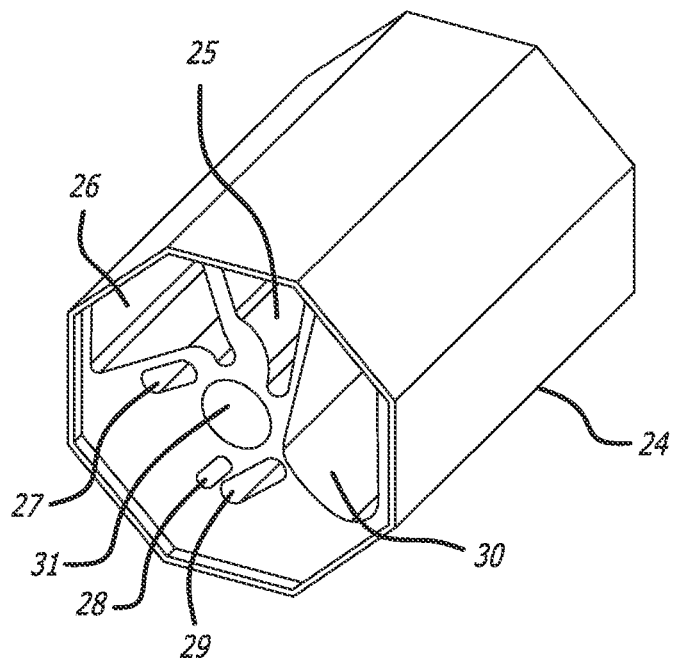
FIG. 4 is a perspective schematic view of part of an assay device of some arrangements.
Figure 5:
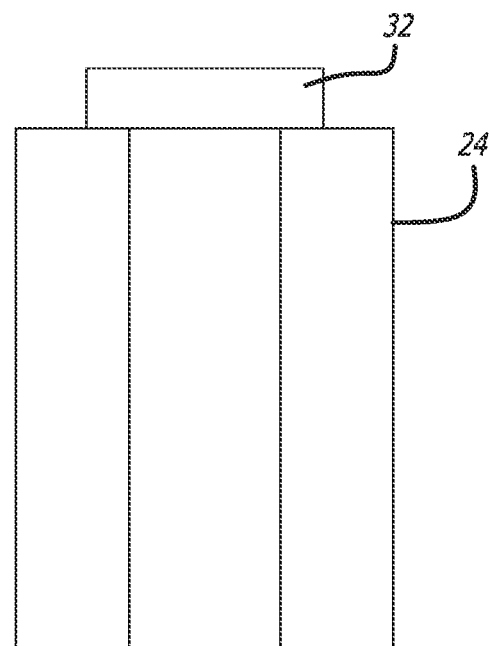
FIG. 5 is a side view of the part of the assay device shown in FIG. 4.
Figure 6:
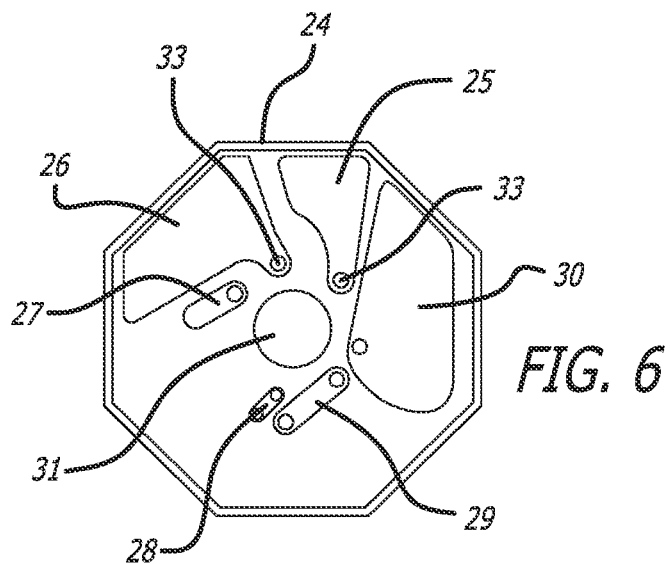
FIG. 6 is an end view of the part of the assay device shown in FIG. 4.

Referring now to FIGS. 4-6 of the accompanying drawings, the assay device 2 comprises a body portion 24 which is elongate and which defines at least one internal chamber. In this arrangement, the body portion 24 has sides which are defined by eight generally planar surfaces which are arranged such that the body portion 24 has an octagonal cross-section. It is, however, to be appreciated that other arrangements incorporate a body portion having a different shape and different cross-section.

In this arrangement, the body portion 24 defines a plurality of internal chambers. In this arrangement; the body portion 24 defines six internal chambers; a sample chamber 25, a wash chamber 26, a lysing agent chamber 27, a liquid reagent chamber 28, a dry reagent chamber 29 and a waste chamber 30. The body portion 24 is also provided with a central aperture 31.

The number of chambers within the assay device can vary in different arrangements from 1 to as many as 10. In an arrangement for an SARS-CoV-2 assay, the assay device 2 comprises six chambers.

One end of the body portion 24 is provided with a protrusion 32, as shown in FIG. 5. The protrusion 32 is provided with a plurality of apertures 33, as shown in FIG. 6. Each aperture 33 provides a fluid communication path with a respective one of the chambers 25-30.

Figure 7:
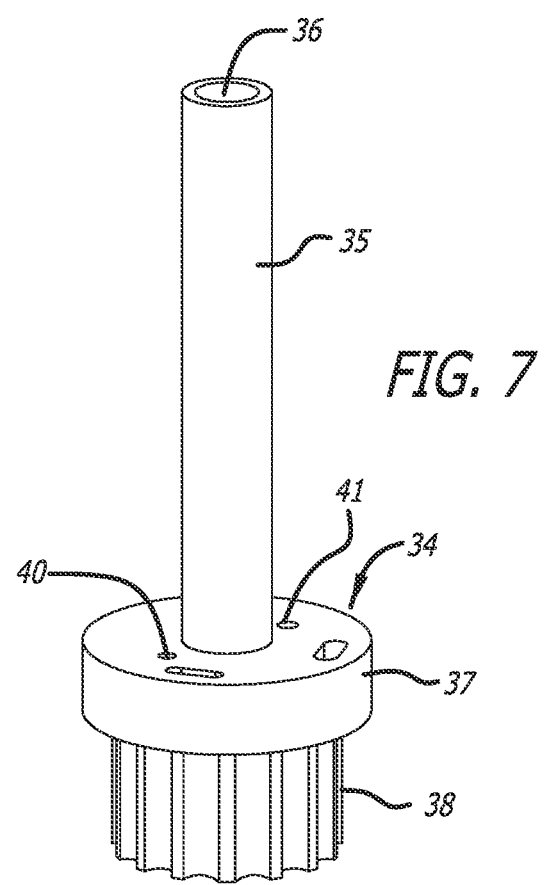
FIG. 7 is a schematic drawing of part of an assay device of some arrangements.

Referring now to FIG. 7 of the accompanying drawings, the assay device 2 comprises a transfer apparatus 34 which is movably mounted to the body portion 24. The transfer apparatus 34 comprises a plunger column 35 which defines an elongate transfer chamber 36. In this arrangement, the plunger column 35 is an elongate and generally cylindrical column which is configured to be at least partly received within the central aperture 31 of the assay device body 24.

The plunger column 35 is the central part of the assay device 2. It is also how the liquid contained in the assay device 2 is moved and manipulated to and from the various chambers as it goes through all the stages of preparation for PCR. The transfer chamber 36 contains a piston 22 in the form of a rubber plunger tip that connects to a plunger 19 contained within the housing 3 of the system 1. Liquid is drawn into the transfer chamber 36 via negative pressure before being forced out of the transfer chamber 36 towards its destination chamber via positive pressure.

The transfer apparatus 34 comprises an enlarged end 37. In this arrangement, the enlarged end 37 is generally cylindrical and is provided with a drive formation in the form of teeth 38 which are provided at spaced apart positions around the enlarged end 37. The teeth 38 are configured to engage a corresponding drive formation on the system 1 such that rotation of the corresponding drive formation of the system 1 rotates the transfer apparatus 34. The movement of the transfer apparatus is controlled by a motor contained within the housing of the system 1. The motor is a brushless DC motor, a stepper motor or any sort of electronically driven motor.

Figure 9:
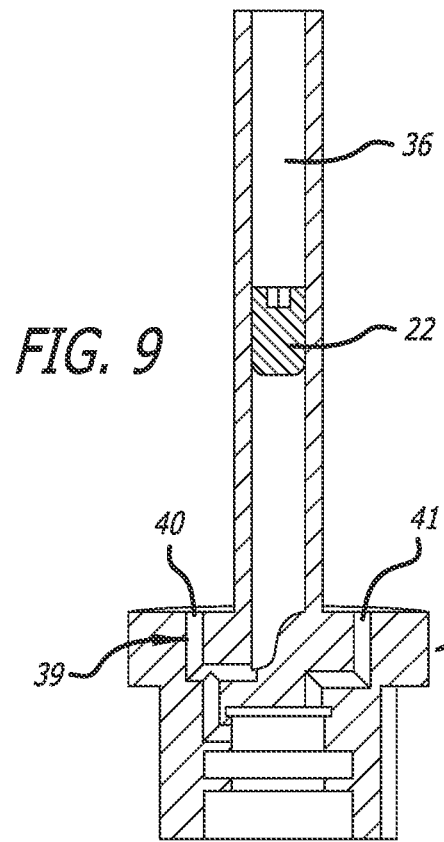
FIG. 9 is a cross-sectional view of the part of the assay device shown in FIG. 7.

Referring now to FIGS. 8 and 9 of the accompanying drawings, the transfer apparatus 34 comprises a moveable flow path 39 which is defined by internal passages within the enlarged end 37. The moveable flow path 39 is configured to move with the transfer apparatus 34 relative to the assay device body 24. The transfer apparatus 34 is provided with flow apertures 40, 41 which are fluidly coupled to the moveable flow path 39. The flow apertures 40, 41 are positioned such that the flow apertures 40, 41 are selectively aligned with the apertures 33 on the assay device body 24 in order to selectively fluidly couple each respective chamber 25-30 to the moveable flow path 39 depending on the position of the transfer apparatus 34 relative to the assay device body 24.

One of the flow apertures 40 is fluidly coupled with the transfer chamber 36 to permit fluid to flow into or out from the transfer chamber 36 when the piston 22 is moved along at least part of the length of the transfer chamber 36 due to the positive or negative pressure produced within the transfer chamber 36 as a result of the movement of the piston 22.

The transfer apparatus 34 comprises a filtration arrangement 42 which is provided within the enlarged end 37 such that fluid flowing along the moveable flow path 39 passes through the filtration arrangement 42. In this arrangement, the filtration arrangement 42 comprises an array of filters, gaskets and microbeads designed to separate larger pollutants from the cells contained in the sample and trap the cells within a "lysing area".

Figure 10:
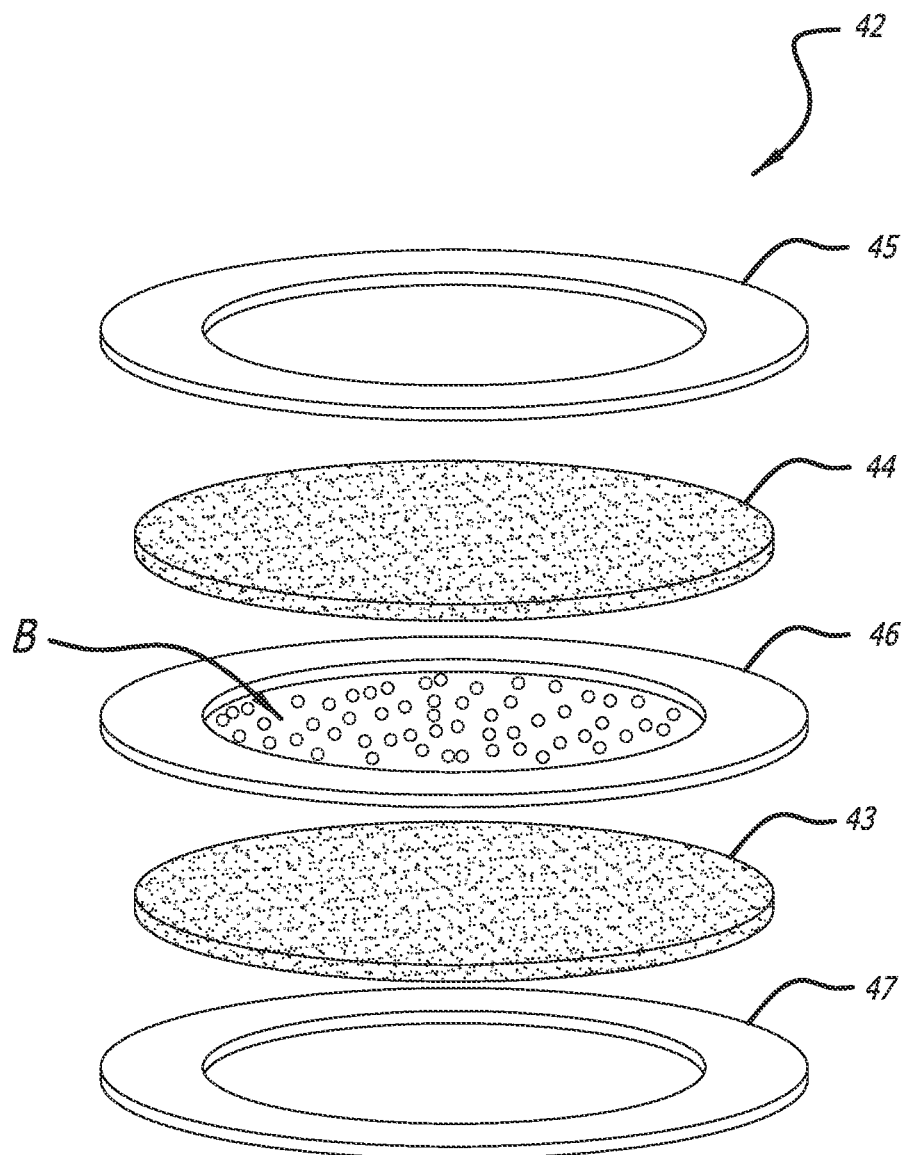
FIG. 10 is a schematic diagram of the components of a filtration arrangement of some arrangements.

Referring to FIG. 10 of the accompanying drawings, the filtration arrangement 42 comprises at least one filter element. In this arrangement, the filtration arrangement 42 comprises a first filter element 43 which is provided with pores of between 2 µm and 30 µm in diameter designed to filter out pollutants such as hair or dust. In this arrangement, the filtration arrangement 42 comprises a second filter element 44 which is superimposed on the first filter element 43, The second filter element 44 is provided with pores of between 0.1 µm and 5 µm in diameter where the pore size is selected to be slightly smaller than the average size of the target cells so they are unable to pass through the second filter element 44.

In this arrangement, the filtration arrangement 42 comprises gaskets 45-47 which provide seals around the filter elements 43, 44. In this arrangement, a larger gasket (approximately 200 µm thick) is provided between the first and second filter elements 43, 44 to create space between the first and second filter for the lysing area.

In this arrangement, the filtration arrangement 42 comprises a plurality of beads B which are retained between the first filter element 43 and the second filter 44. In some arrangements, the beads B are microbeads having a diameter of approximately 100 microns. In some arrangements, approximately half of the beads B are buoyant so they collect near the top of the filter arrangement 42 during sonication and the other half are designed to not be buoyant and collect near the bottom of the filter arrangement 42. Between the two types of beads, a majority of the lysing area will be filled with microbeads that help disrupt cell membranes during sonication.

Figure 11:
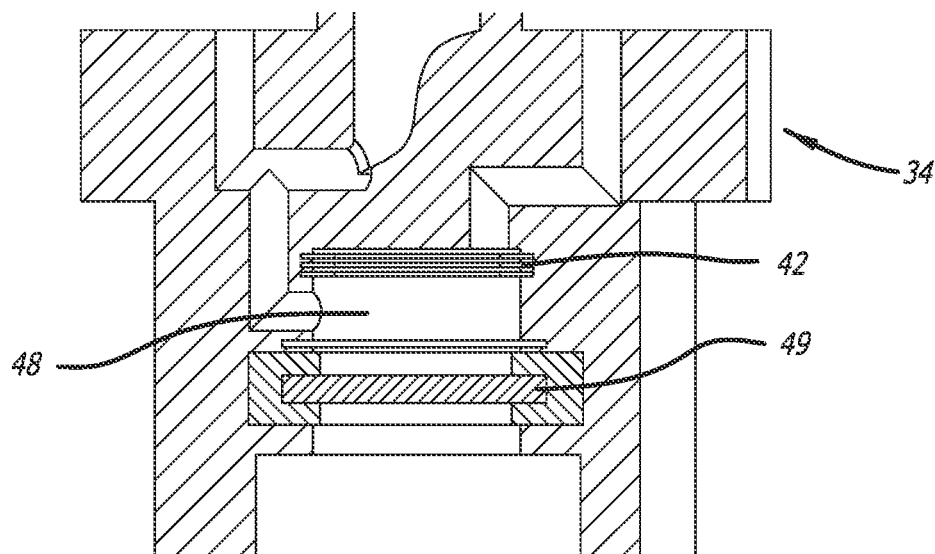
FIG. 11 is a schematic drawing of part of an assay device of some arrangements.

Referring now to FIG. 11 of the accompanying drawings, the transfer apparatus 34 comprises a sonication chamber 48 which is positioned adjacent to the filtration arrangement 42 and which is fluidly coupled to the moveable flow path 39. In some arrangements, the sonication chamber 48 has a volume of between 100 µl to 1000 µl. In some arrangements, the inlet to the sonication chamber 48 is positioned at a level below the outlet of the sonication chamber 48, when the assay device 2 is standing upright, to allow liquid to flow from low to high and to let any air bubbles escape in the process.

The filtration arrangement 42 is provided within the sonication chamber and an ultrasonic transducer 49 is provided at the one end of the sonication chamber 48. In some arrangements, the filtration arrangement 42 separates the inlet area of the sonication chamber 48 from the outlet area of the sonication chamber 48, substantially between on half or one quarter of the distance between the inlet and the outlet of the sonication chamber 48.

The ultrasonic transducer 49 is coupled electrically to the controller 23 of the system 1 when the assay device 2 is inserted into the system 1. The ultrasonic transducer 49 is configured to be controlled by the controller 23. The controller 23 comprises a processor configured to control at least one process of the system and a memory, the memory storing executable instructions which, when executed by the processor, cause the processor to provide an output to perform the at least one process. The memory of the controller 23 stores executable instructions which, when executed by the processor, cause the processor to control the ultrasonic transducer 49 to oscillate at a selected frequency in order to lyse cell within the sonication chamber 48 to release nucleic add (DNA/RNA) from the cells.

In some arrangements, the ultrasonic transducer 49 is at least partly of a compound comprising lead, zirconium and titanium. The compound of the ultrasonic transducer 49 is selected to provide the ultrasonic transducer 49 with the properties for it to oscillate at a frequency of 2.8 MHz to 3.2 MHz. This frequency range is the preferred frequency range for the ultrasonic transducer 49 to produce ultrasonic waves which lyse or rupture cells.

In some arrangements, the ultrasonic transducer 49 comprises a first electrode on an upper side and a second electrode on a lower side which is on the opposing side of the ultrasonic transducer 49. In some arrangements, the first electrode and the second electrode comprise silver, for instance in the form of silver stamp paint. In some arrangements, the capacitance between the first electrode and the second electrode is 800 pF to 1300 pF.

In some arrangements, the first electrode on the upper side of the ultrasonic transducer 49 is at least partly covered with a glass coating. The glass coating minimizes or prevents possible contamination of liquid within the sonication chamber 48 by the material of the first electrode. The glass coating also minimizes or prevents erosion of the silver of the first electrode, for instance due to cavitation bubble collapse caused by ultrasonic waves travelling through liquid within the sonication chamber 48 when the system is in use.

The first and second electrodes of the ultrasonic transducer 49 are connected electrically to respective first and second electrical terminals of the controller 23.

In some arrangements, the controller 23 comprises an AC driver. The AC driver generates an AC drive signal at a predetermined frequency and outputs the AC drive signal to drive the ultrasonic transducer 49. The AC driver comprises a circuit incorporating electronic components which are connected to generate an AC drive signal from power received from a power source. In some arrangements, the AC driver comprises a H-bridge circuit. In some arrangements, the H-bridge circuit comprises four MOSFETs which are connected to convert a direct current into an alternating current at high frequency (e.g. a frequency in the range 2.8 MHz to 3.2 MHz).

In some arrangements, the controller 23 comprises an active power monitor. The active power monitor comprises an electronic circuit which monitors the active power used by the ultrasonic transducer 49 when the ultrasonic transducer 49 is driven by the AC drive signal. The active power monitor provides a monitoring signal which is indicative of an active power used by the ultrasonic transducer 49. In some arrangements, the active power monitor comprises a current sensor which senses a drive current of the AC drive signal driving the ultrasonic transducer 49 and provides a monitoring signal which is indicative of the sensed drive current.

The processor of the controller 23 controls the AC driver and receives the monitoring signal from the active power monitor.

In some arrangements, the controller 23 comprises a frequency controller which is implemented in the executable code stored in the memory which, when executed by the processor, cause the processor to perform at least one function of the frequency controller.

The memory of the controller 23 stores executable instructions which, when executed by the processor, cause the processor to control the ultrasonic transducer 49 to oscillate at a plurality of frequencies within a predetermined sweep frequency range and to select a drive frequency for the ultrasonic transducer 49 which is between a first predetermined frequency and a second predetermined frequency for lysing cells within the sonication chamber 48.

In some arrangements, the frequency will be determined by the type of cells that are being lysed as some cells may require different frequencies due to their physical characteristics (size, shape, presence of cell wall, etc.).

There is an optimum frequency or frequency range for lysing cells within the sonication chamber. The optimum frequency or frequency range will depend on at least the following four parameters:

1. Transducer Manufacturing Processes

In some arrangements, the ultrasonic transducer 49 comprises a piezoelectric ceramic. The piezoelectric ceramic is manufactured by mixing compounds to make a ceramic dough and this mixing process may not be consistent throughout production. This inconsistency can give rise to a range of different resonant frequencies of the cured piezoelectric ceramic.

If the resonant frequency of the piezoelectric ceramic does not correspond to the required frequency of operation, the process of lysing cells is not optimal. Even a slight offset in the resonant frequency of the piezoelectric ceramic is enough to impact the lysing process, meaning that the system will not function optimally.

2. Load on Transducer

During operation, any changes in the load on the ultrasonic transducer 49 will inhibit the overall displacement of the oscillation of the ultrasonic transducer 49. To achieve optimal displacement of the oscillation of the ultrasonic transducer 49, the drive frequency must be adjusted to enable the controller 23 to provide adequate power for maximum displacement.

The types of loads that can affect the efficiency of the ultrasonic transducer 49 can include the amount of liquid on the transducer (i.e. the amount of liquid within the sonication chamber 48).

3. Temperature

Ultrasonic oscillations of the ultrasonic transducer 49 are partially damped by its assembly in the assay device 2. This dampening of the oscillations can cause a rise in local temperatures on and around the ultrasonic transducer 49.

An increase in temperature affects the oscillation of the ultrasonic transducer 49 due to changes in the molecular behavior of the ultrasonic transducer 49. An increase in the temperature means more energy to the molecules of the ceramic, which temporarily affects its crystalline structure. Although the effect is reversed as the temperature reduces, a modulation in supplied frequency is required to maintain optimal oscillation.

An increase in temperature also reduces the viscosity of the solution within the sonication chamber 48, which may require an alteration to the drive frequency to optimize lysis of cells within the sonication chamber 48.

4. Distance to Power Source

The oscillation frequency of the ultrasonic transducer 49 can change depending on the wire-lengths between the ultrasonic transducer 49 and the oscillator-driver. The frequency of the electronic circuit is inversely proportional to the distance between the ultrasonic transducer 49 and the controller 23.

Although the distance parameter is primarily fixed in this arrangement, it can vary during the manufacturing process of the system 1. Therefore, it is desirable to modify the drive frequency of the ultrasonic transducer 49 to compensate for the variations and optimize the efficiency of the system.

Figure 12:
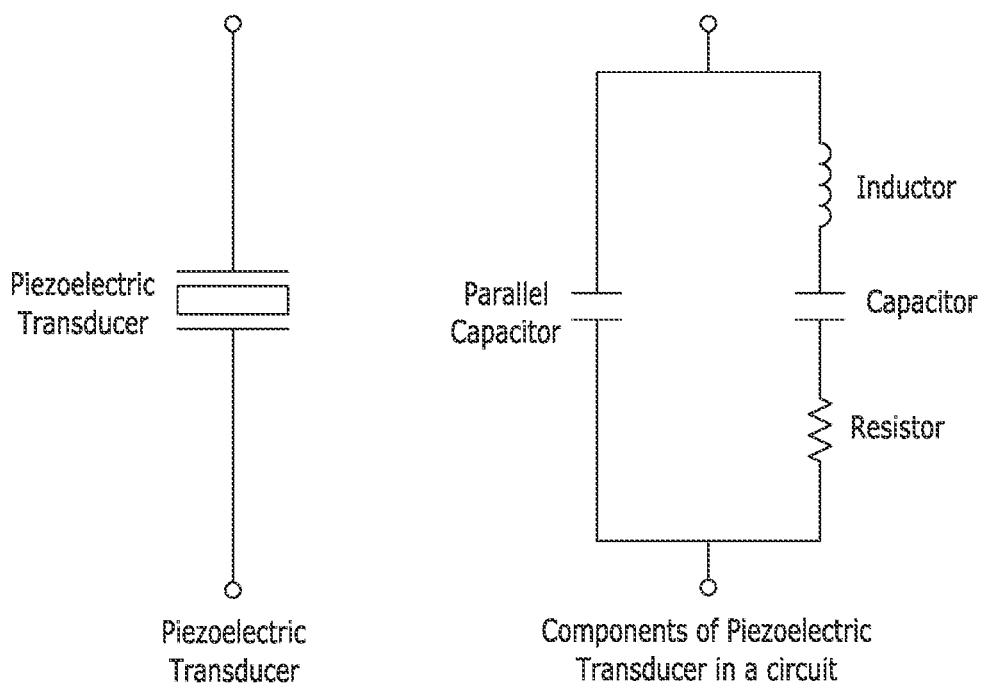
FIG. 12 is schematic diagram showing a piezoelectric transducer modelled as an RLC circuit.

An ultrasonic transducer 49 can be modelled as an RLC circuit in an electronic circuit, as shown in FIG. 12. The four parameters described above may be modelled as alterations to the overall inductance, capacitance, and/or resistance of the RLC circuit, changing the resonance frequency range supplied to the transducer. As the frequency of the circuit increases to around the resonance point of the transducer, the log Impedance of the overall circuit dips to a minimum and then rises to a maximum before settling to a median range.

Figure 13:
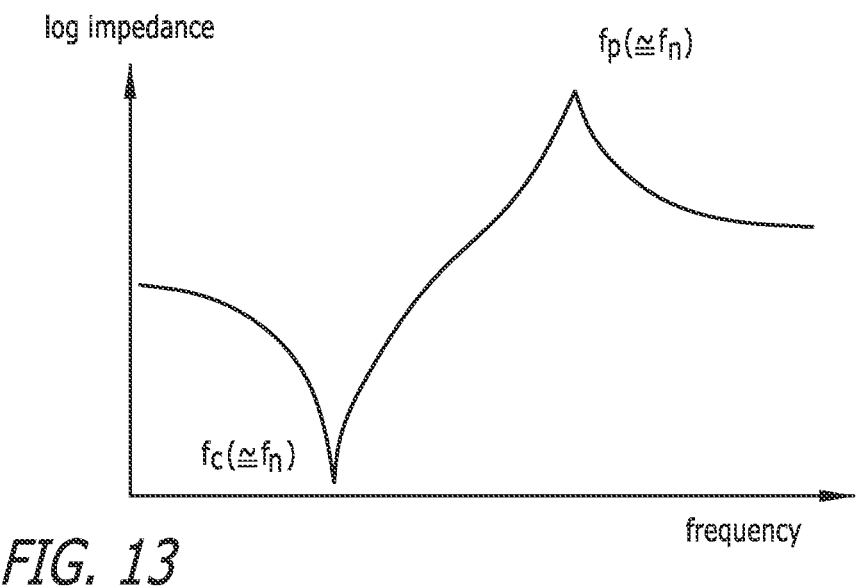
FIG. 13 is graph of frequency versus log impedance of an RLC circuit.
Figure 14:
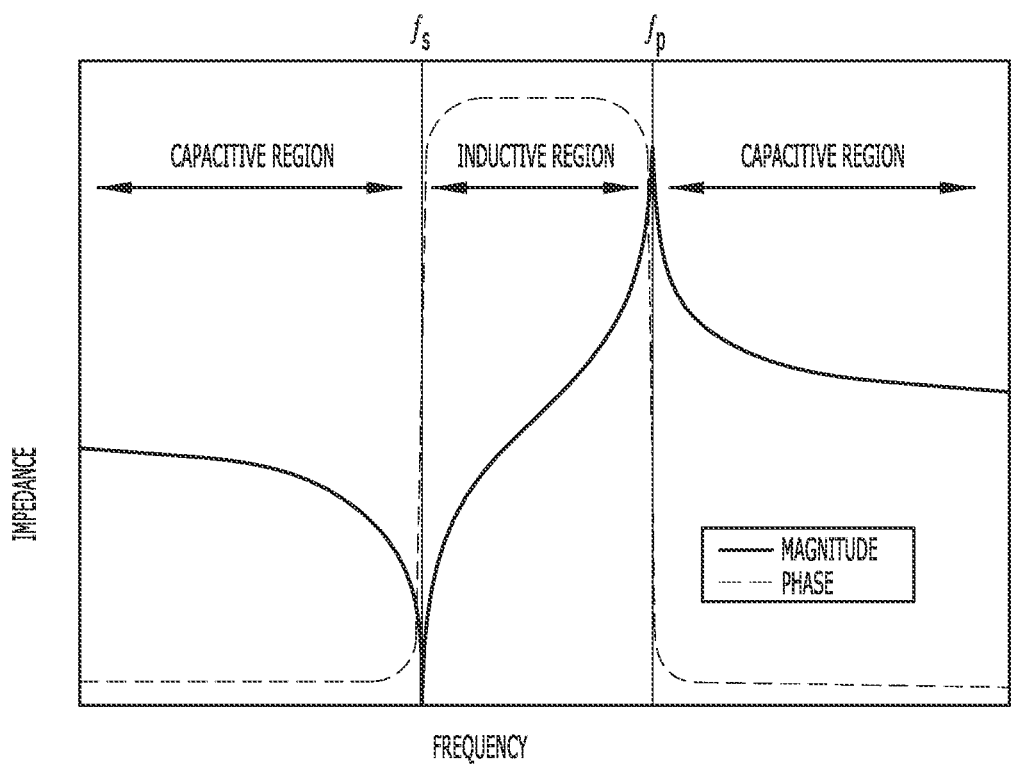
FIG. 14 is graph of frequency versus log impedance showing inductive and capacitive regions of operation of a piezoelectric transducer.

FIG. 13 shows a generic graph explaining the change in overall impedance with increase in frequency in the RLC circuit. FIG. 14 shows how a piezoelectric transducer acts as a capacitor in a first capacitive region at frequencies below a first predetermined frequency $f_s$ and in a second capacitive region at frequencies above a second predetermined frequency $f_p$. The piezoelectric transducer acts as an inductor in an inductive region at frequencies between the first and second predetermined frequencies $f_s$, $f_p$. In order to maintain optimal oscillation of the transducer and hence maximum efficiency, the current flowing through the transducer must be maintained at a frequency within the inductive region.

The memory of the controller 23 stores executable instructions which, when executed by the processor, cause the processor to maintain the frequency of oscillation of the ultrasonic transducer 49 within the inductive region, in order to maximize the efficiency of the lysis of cells within the sonication chamber 48.

The memory of the controller 23 stores executable instructions which, when executed by the processor, cause the processor to perform a sweep operation in which the controller 23 drives the transducer at frequencies which track progressively across a predetermined sweep frequency range. In other words, the driver apparatus 2 drives the transducer at a plurality of different frequencies across the predetermined sweep frequency range. For instance at frequencies which increment by a predetermined frequency from one end of the sweep frequency range to the other end of the sweep frequency range.

In some arrangements, as the controller 23 performs the sweep, the controller 23 monitors an Analog-to-Digital Conversion (ADC) value of an Analog-to-Digital converter which is provided within the controller 23 and coupled to the ultrasonic transducer 49. In some arrangements the ADC value is a parameter of the ADC which is proportional to the voltage across the ultrasonic transducer 49. In other arrangements, the ADC value is a parameter of the ADC which is proportional to the current flowing through the ultrasonic transducer 49.

During the sweep operation; the controller 23 locates the inductive region of the frequency for the transducer. Once the controller 23 has identified the inductive region, the controller 23 records the ADC value and locks the drive frequency of the transducer at a frequency within the inductive region (i.e. between the first and second predetermined frequencies $f_s$, $f_p$) in order to optimize the operation of the ultrasonic transducer 49. When the drive frequency is locked within the inductive region, the electro-mechanical coupling factor of the transducer is maximized, thereby maximizing the operation of the ultrasonic transducer 49.

In some arrangements, the controller 23 determines the active power being used by the ultrasonic transducer 49 by monitoring the current flowing through the transducer 49. The active power is the real or true power which is dissipated by the ultrasonic transducer 49.

Ultrasonic (piezoelectric) transducer mechanical deformation is linked to the AC Voltage amplitude that is applied to it, and in order to guarantee optimal functioning and delivery of the system, the maximum deformation must be supplied to the ultrasonic transducer all the time. By Pulse Width Modulation (PWM) of the AC voltage applied to the ultrasonic transducer, the mechanical amplitude of the vibration remains the same. In some arrangements, the system actively adjusts the duty cycle of the AC voltage waveform to maximize deformation of the ultrasonic transducer in order to guarantee optimal functioning and delivery of the system.

One approach involves modifying the AC voltage applied to the ultrasonic transducer via the use of a Digital to Analog Converter (DAC). The energy transmitted to the ultrasonic transducer would be reduced but so would the mechanical deformation which as a result does not produce maximum deformation. The RMS voltage applied to the ultrasonic transducer would be the same with effective Duty Cycle modulation as with Voltage modulation, but the active power transferred to the ultrasonic transducer would degrade. Indeed, given the formula below:

Active Power displayed to the ultrasonic transducer being:

$$Pa = \frac{2\sqrt{2}}{\pi} Irms * Vrms * \cos\varphi,$$

Where
$\varphi$ is the shift in phase between current and voltage
$I_{rms}$ is the root mean square Current
$V_{rms}$ is the root mean square Voltage.

When considering the first harmonic, Irms is a function of the real voltage amplitude applied to the ultrasonic transducer, as the pulse width modulation alters the duration of voltage supplied to the ultrasonic transducer, controlling Irms.

In this arrangement, the memory of the controller 23 stores instructions which, when executed by the processor of the controller 23, cause the processor to:

A. control the AC driver of the controller 23 to output an AC drive signal to the ultrasonic transducer 49 at a predetermined sweep frequency;

B. calculate the active power being used by the ultrasonic transducer 49 based on the monitoring signal;

C. control the AC driver to modulate the AC drive signal to maximize the active power being used by the ultrasonic transducer 49;

D. store a record in the memory of the maximum active power used by the ultrasonic transducer 49 and the sweep frequency of the AC drive signal;

E. repeat steps A-D for a predetermined number of iterations with the sweep frequency incrementing with each iteration such that, after the predetermined number of iterations has occurred, the sweep frequency has been incremented from a start sweep frequency to an end sweep frequency;

F. identify from the records stored in the memory the optimum frequency for the AC drive signal which is the sweep frequency of the AC drive signal at which a maximum active power is used by the ultrasonic transducer 49; and G. control the AC driver to output an AC drive signal to the ultrasonic transducer 49 at the optimum frequency.

In some arrangements, the start sweep frequency is 2800 kHz and the end sweep frequency is 3200 kHz. In other arrangements, the start sweep frequency and the end sweep frequency are lower and upper frequencies of a frequency range within the range of 2800 kHz to 3200 kHz.

In some arrangements, the processor controls the AC driver to output an AC drive signal to the ultrasonic transducer 49 at frequency which is shifted by between 1-10% of the optimum frequency. In these arrangements, the frequency shift is used to prolong the life of the ultrasonic transducer 49 by minimizing potential damage caused to the ultrasonic transducer 49 when the ultrasonic transducer 49 is driven continuously at the optimum drive frequency which produces maximum displacement.

In some arrangements, the AC driver modulates the AC drive signal by pulse width modulation to maximize the active power being used by the ultrasonic transducer 49.

In some arrangements, the processor 40 controls the AC driver to alternately output an AC drive signal to the ultrasonic transducer 49 at the optimum frequency for a first predetermined length of time and to not output an AC drive signal to the ultrasonic transducer 49 for a second predetermined length of time. This alternate activation and deactivation of the ultrasonic transducer 49 has been found to optimize the process of lysing cells in a sample within the sonication chamber 48.

In some arrangements, in order to ensure optimal operation of the ultrasonic transducer 49, the controller 23 operates in a recursive mode. When the controller 23 operates in the recursive mode, the controller 23 runs the sweep of frequencies in steps A-D periodically during the operation of the system.

In some arrangements, the AC driver of the controller 23 is configured to alternately output the AC drive signal and to not output the AC drive signal according to an operating mode. The timings of twelve operating modes of some arrangements are shown in Table 1 below.

TABLE 1

| Operating mode | First predetermined length of time (seconds) | Second predetermined length of time (seconds) |
| --- | --- | --- |
| 1 | 4 | 2 |
| 2 | 3 | 2 |
| 3 | 2 | 2 |
| 4 | 1 | 2 |
| 5 | 1 | 1 |
| 6 | 2 | 1 |
| 7 | 3 | 1 |
| 8 | 4 | 1 |
| 9 | 4 | 3 |
| 10 | 3 | 3 |
| 11 | 2 | 3 |
| 12 | 1 | 3 |

In some arrangements, the memory of the controller 23 stores executable instructions which, when executed by the processor, cause the processor to perform the sweep operation to locate the inductive region each time the oscillation is started or re-started. In these arrangements, the memory of the controller 23 stores executable instructions which, when executed by the processor, cause the processor to lock the drive frequency at a new frequency within the inductive region each time the oscillation is started and thereby compensate for any changes in the parameters that affect the efficiency of operation of the ultrasonic transducer 49.

In some arrangements, in order to ensure optimal operation of the ultrasonic transducer 49, the controller 23 operates in a recursive mode. When the controller 23 operates in the recursive mode, the controller 23 runs the sweep of frequencies periodically during the operation of the system and monitors the ADC value to determine if the ADC value is above a predetermined threshold which is indicative of optimal oscillation of the operation of the ultrasonic transducer 49.

In some arrangements, the controller 23 runs the sweep operation while the system is in the process of lysing cells in case the controller 23 is able to identify a possible better frequency for the ultrasonic transducer 49 which maximizes displacement of the ultrasonic transducer 49. If the controller 23 identifies a better frequency, the controller 23 locks the drive frequency at the newly identified better frequency in order to maintain optimal operation of the ultrasonic transducer 49.

Figure 15:
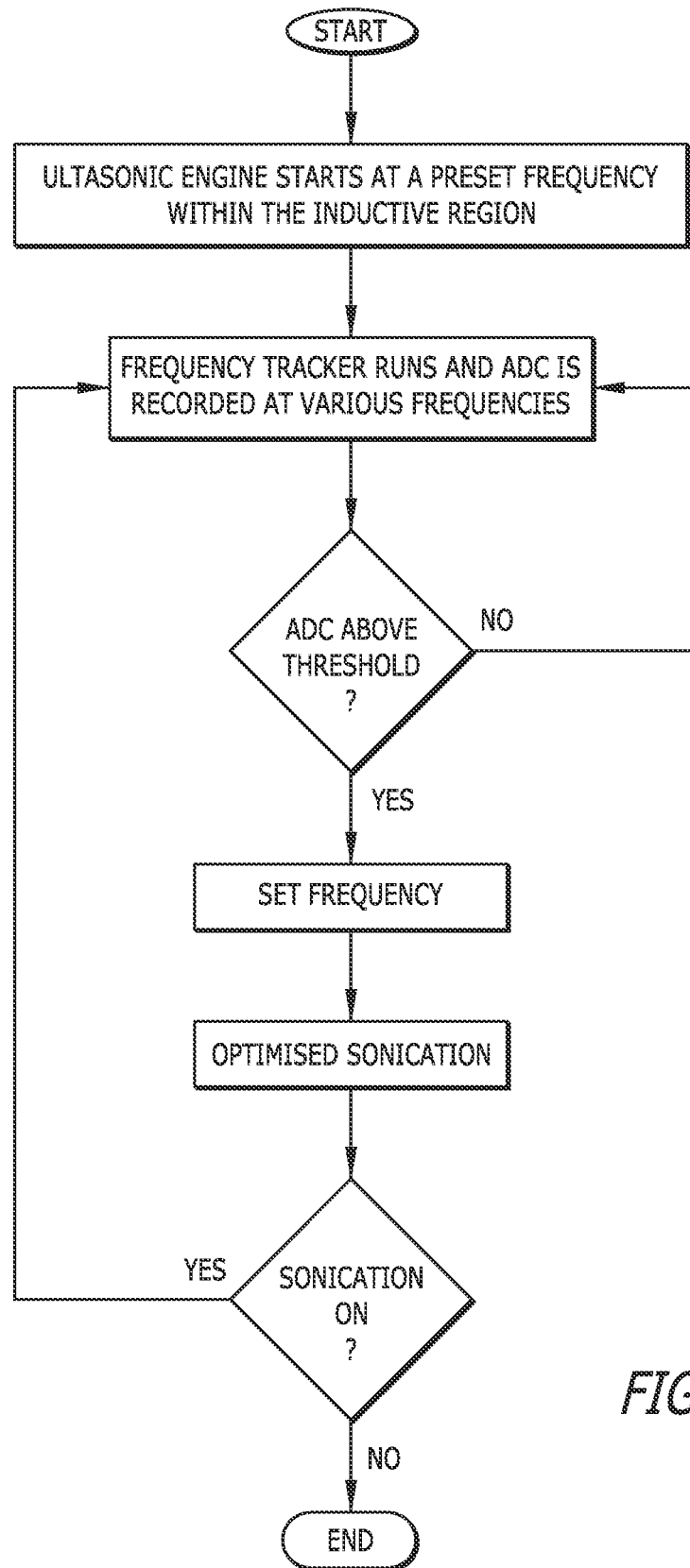
FIG. 15 is flow diagram showing the operation of a controller of some arrangements.

FIG. 15 shows a flow diagram of the operation of the controller 23 of some arrangements.

Figure 16:
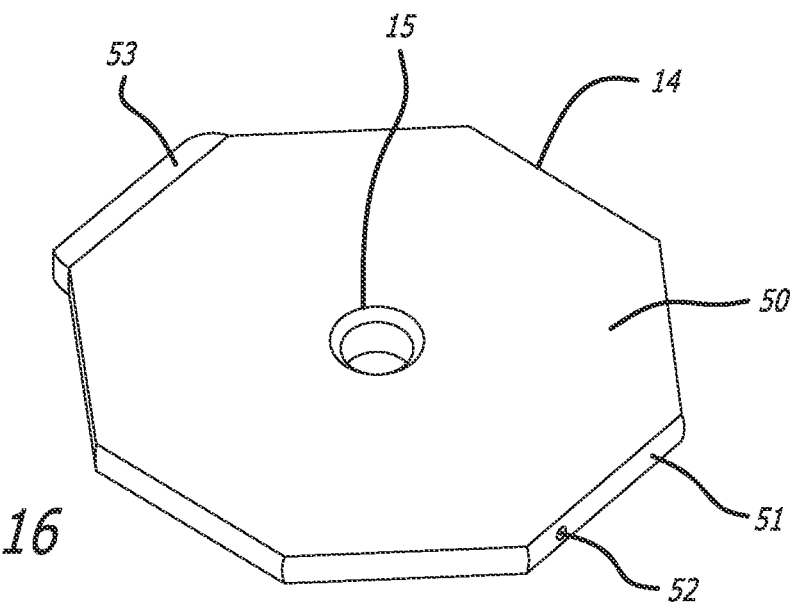
FIG. 16 is a perspective view of part of an assay device of some arrangements.
Figure 17:
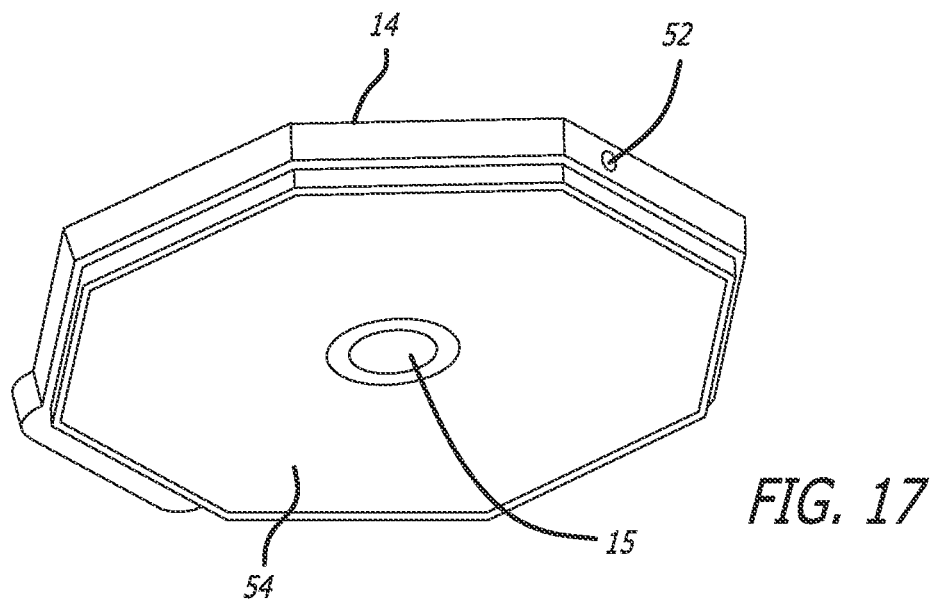
FIG. 17 is a perspective view of part of an assay device of some arrangements.

Referring now to FIGS. 16 and 17 of the accompanying drawings, the lid 14 of the assay device 2 comprises a generally planar cover 50 which is configured to close an open end of at least the sample chamber 25 of the assay device body 24. The lid 14 comprises side walls 51 which extend around the periphery of the cover 50. In this arrangement, an air inlet aperture 52 is provided in one of the side walls 51.

In this arrangement, the lid 14 comprises a pivotal mounting arrangement 53 for pivotally mounting the lid 14 to the assay device body 24. In other arrangements, the lid 14 is configured with a different movable mounting arrangement to moveably mount the lid 14 to the assay device body 24.

The lid 14 comprises a gas permeable membrane 54 which is superimposed beneath the lid member 50 around the ends of the side walls 51. The gas permeable membrane 54 provides a substantially gas tight seal around the side walls 51 and around the central aperture 15 to prevent cross contamination or accidental spillage. In some arrangements, the gas permeable membrane 54 is a Gore-Tex™ material.

In use, the air inlet aperture 52 allows air to flow into the lid 14 and for the air to flow through the gas permeable membrane 54 and into at least the sample chamber 25 within the assay device body 24.

In other arrangements, the gas permeable membrane 54 may be replaced with another one-way gas flow member, such as a valve.

Figure 18:
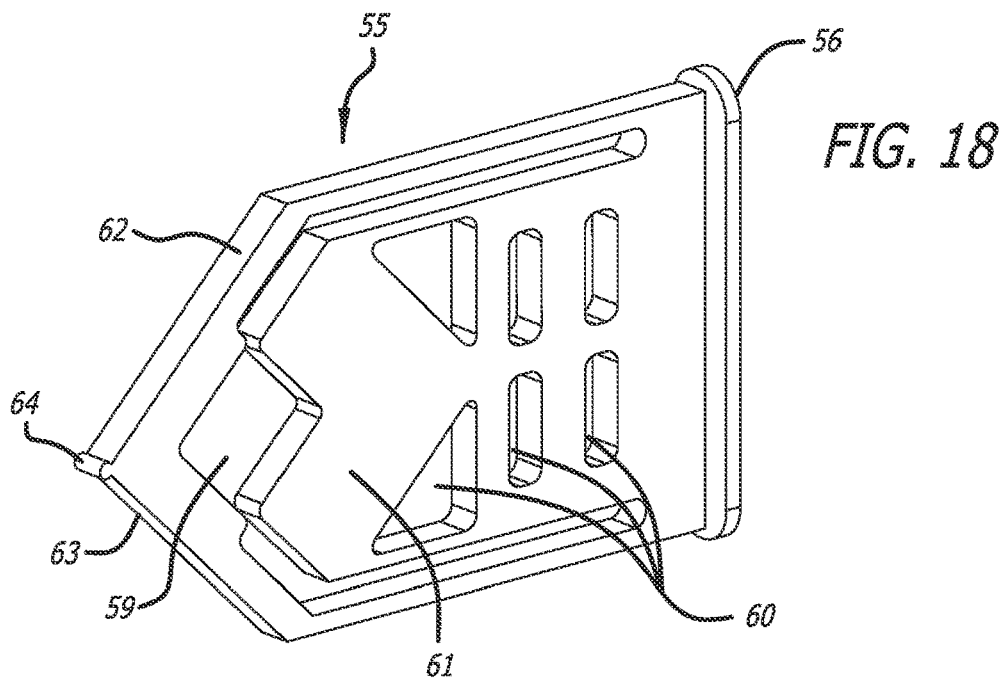
FIG. 18 is a perspective view of part of an assay device of some arrangements.
Figure 19:
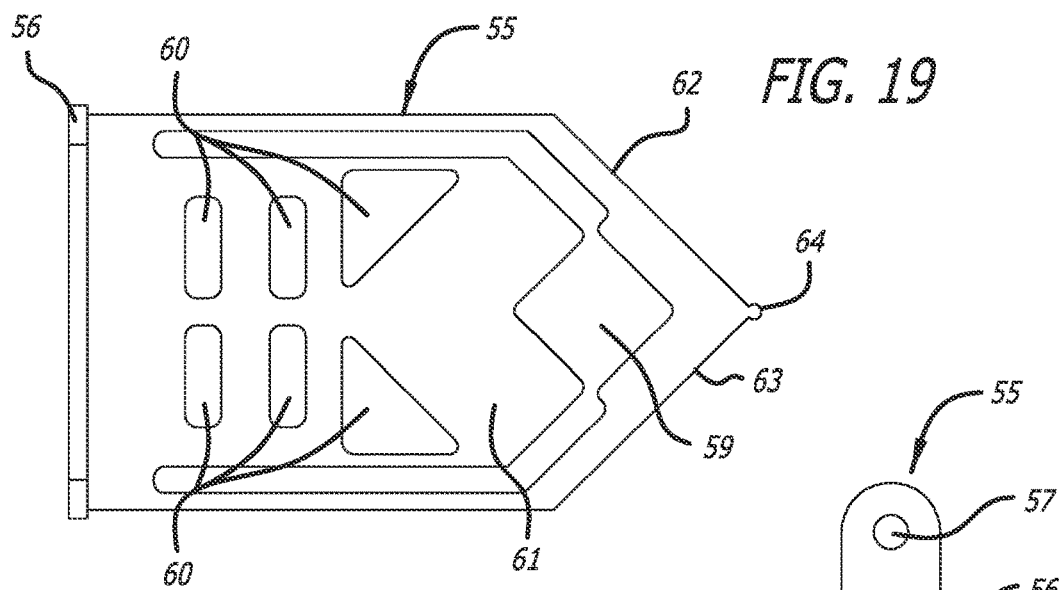
FIG. 19 is a side view of the part of the assay device shown in FIG. 18.
Figure 20:
FIG. 20 is an end view of the part of the assay device shown in FIG. 18.

Referring now to FIGS. 18-20 of the accompanying drawings, the PCR apparatus 16 of the assay device 2 comprises a fin 55 which is coupled to the assay device body 24 such that the fin 55 protrudes outwardly from the assay device body 24. The fin 55 comprises an enlarged mounting member 56 which is configured to be connected to the assay device body 24. The mounting member 56 is provided with a first aperture 57 and a second aperture 58 which extend through to the fin 55 such that the apertures 57, 58 are in fluid communication with a PCR chamber 59 which is defined within the fin 55. In this arrangement, the fin 55 further comprises a plurality of internal chambers 60 in a central portion 61 which partly surrounds the PCR chamber 59.

The fin 55 is generally rectangular with angled ends 62, 63 which converge to a point 64. In use, after the sample passes through both the reagent chambers of the assay device 2, it is pushed into the PCR fin 55 which contains the PCR chamber 59.

In some arrangements, the reagents selected for the PCR process are chosen in order to facilitate an extreme rRT-PCR process as well as allow for temperature monitoring via fluorescence. In some arrangements, the reagent formula consists of or comprises: 5 µM of each forward and reverse primer (6 total primers, 2 sets for detecting SARS-CoV-2 and 1 set to serve as a control for a successful PCR reaction), IX LCGreen+ dye, 0.2 µM of each deoxynucleoside triphosphate (dNTP): dATP, dTTP, dGTP, dCTP, 50 mM Tris, 1.65 µM KlenTaq, 25 ng/µL BSA, 1.25 U/µL Malone Murine leukemia virus reverse transcriptase (MMLV), 7.4 mM $MgCl_2$, and sulforhodamine B.

Figure 21:
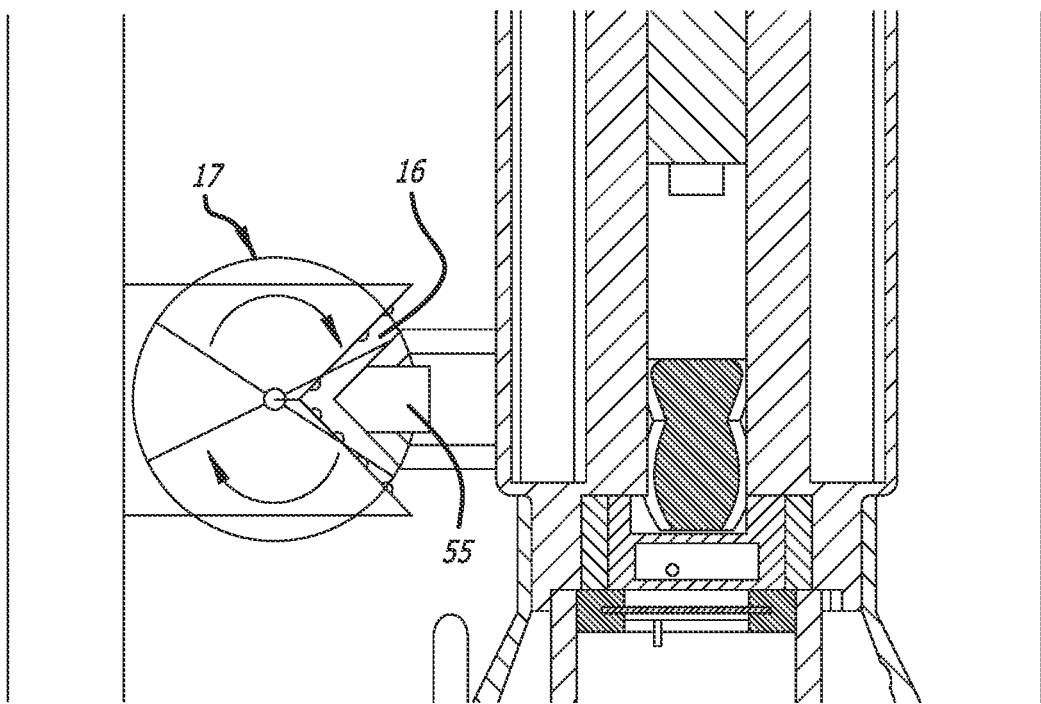
FIG. 21 is a cross-sectional view of part of a system of some arrangements and part of an assay device of some arrangements.
Figure 22:
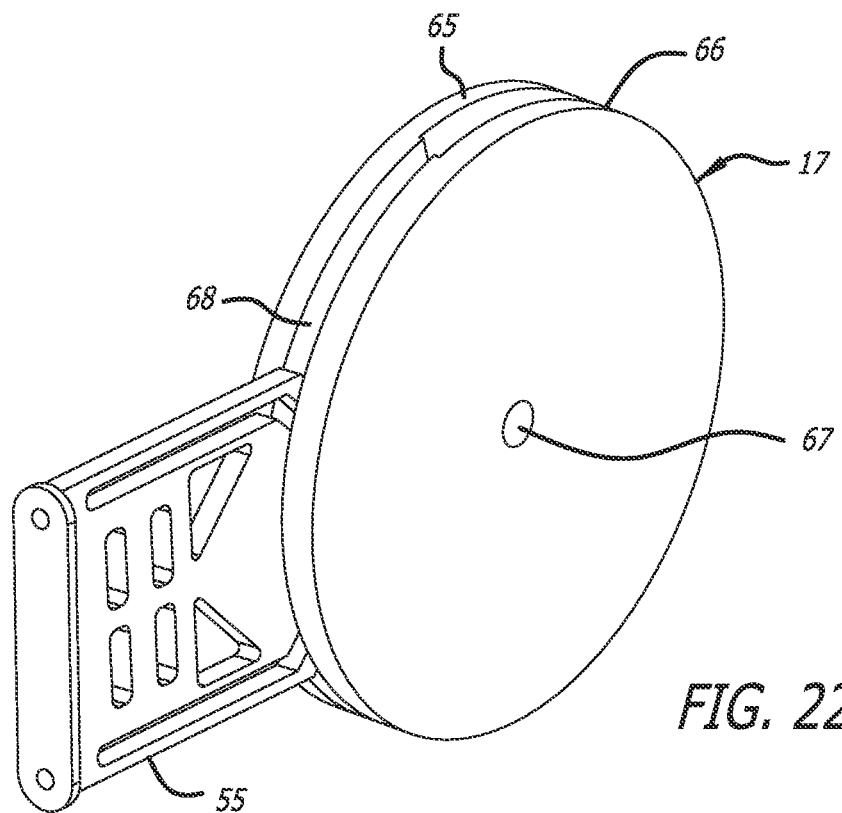
FIG. 22 is a perspective view of part of a system of some arrangements and part of an assay device of some arrangements.

Referring now to FIGS. 21 and 22 of the accompanying drawings, the fin 55 of the PCR apparatus 16 is configured to be at least partly received within the heating apparatus 17.

In this arrangement, the heating apparatus 17 comprises two generally circular planar discs 65, 66 which are spaced apart from one another and rotatably mounted to a pivot member 67. A heating recess 68 is defined by a part of the space between the discs 65, 66.

Figure 23:
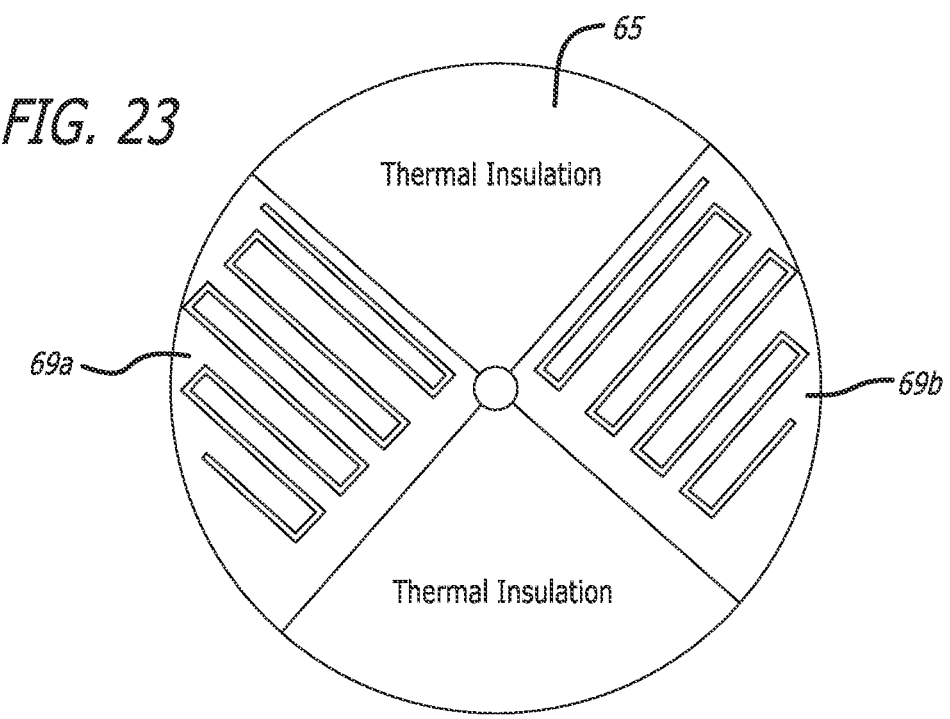
FIG. 23 is a side view of part of an assay device of some arrangements.

In this arrangement, disc 65 is a movable support element which carries a first heating element 69a and a second heating element 69b, as shown in FIG. 23. The first and second heating elements 69a, 69b are spaced apart from one another on either side of the disc 65.

The heating apparatus 17 further comprises a motor which is configured to move the disc 65 to rotate about the pivot member 67 so that the disc 65 moves between a first position in which the first heating element 69a is positioned closer to the heating recess 68 than the second heating element 69b and a second position in which the second heating element 69b is positioned closer to the heating recess 68 than the first heating element 69a. The motor is coupled electrically to the controller 23 so that the controller 23 can control the motor to move the disc 65 cyclically between the first position and the second position.

In some arrangements, the heating apparatus 17 comprises a temperature sensor which is configured to sense the temperature of a liquid within the PCR apparatus positioned within the heating recess 68 and the system is configured to control the movement of the first and second heating elements in response to the sensed temperature.

Figure 24:
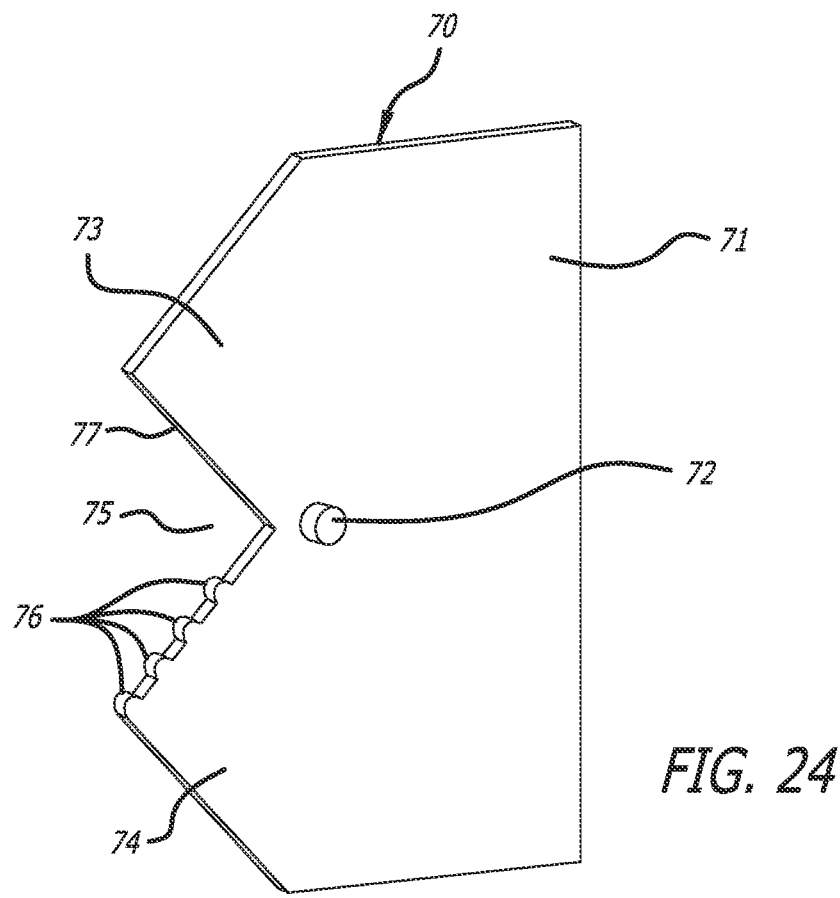
FIG. 24 is a perspective view of part of a system of some arrangements.

Referring now to FIG. 24 of the accompanying drawings, the system 1 comprises an infectious disease detection arrangement in the form of a fluorescence detection arrangement 70 which comprises a generally planar support member 71 which is provided with an aperture 72 through which the pivot member 67 extends. The fluorescence detection arrangement comprises a first triangular portion 73 and a second triangular portion 74 and an indented portion 75. The planar body 71 and the triangular portions 73, 74 are positioned in the space between the discs 65, 66 of the heating apparatus.

The indented portion 75 is shaped to receive the pointed end of the fin 55 of the PCR apparatus 16.

The detection apparatus 70 is provided with a plurality of light emitters 76 along one edge of the recessed portion 75 and a plurality of photo receptors 77 along another edge of the recessed portion 75. In this arrangement, there are four light emitters in the form of four LEDs which are each configured to transmit light at a different wavelength and there are four photo detectors 77 which are each configured to detect light at a different wavelength. However, in other arrangements, there are a different number of light emitters and photo detectors.

The detection apparatus 70 is, in some arrangements, configured to detect the fluorescence emitted from the LCGreen+ and sulforhodamine B dyes to monitor PCR, melting curves and temperature changes.

In some arrangements, the detection apparatus is a SARS-CoV-2 virus detection apparatus detects a presence of the SARS-CoV-2 virus that causes COVID-19 disease.

Result Reporting

In some arrangements, the system 1 comprises a display, such as an LCD monitor, on the exterior of the housing 3. After the information from the system has been processed by the controller 23, the result of the test will be displayed on the display. The four possible results of the assay are as follows: Positive, Negative, Inconclusive, or Invalid. In the case of a COVID-19 test, the criteria for the four results are shown in Table 2 below.

TABLE 2

| COVID Gene1 | COVID Gene2 | RNAse P 'control' | Result | Report |
|---|---|---|---|---|
| + | + | +/− | 2019-nCOV detected | Positive |
| One of two is + | | +/− | Inconclusive | Inconclusive |
| − | − | + | 2019-nCOV not detected | Negative |
| − | − | − | Invalid result | Invalid |

SARS-CoV-2 Example

The operation of a system of some arrangements will now be described for a SARS-CoV-2 assay.

In the assay device 2, the first chamber is the sample chamber into which a user adds a target sample to be screened. In some arrangements, the target sample is a saliva sample or a sputum sample. In other arrangements, the target sample is collected from a user by a nasopharyngeal swab or an oropharyngeal swab. In further arrangements, the target sample is a blood sample.

In some arrangements, the target sample is between 1 ml to 5 ml in volume. The sample, after being collected from the patient, is placed into an elution buffer prior to being added to the sample chamber. In some arrangements, the elution buffer comprises: 1 M Imidazole solution, 1 M Tris, 0.5 M EDTA, Milli-Q or Deionized water.

The next chamber is the wash chamber. In some arrangements, the wash chamber contains an excess amount (3 ml to 5 ml) of an elution buffer as mentioned above. The wash buffer is used to wash the sample to remove any potential contaminants. The next chamber is the lysing agent chamber. In some arrangements, the lysing agent chamber contains a mixture of chemicals to assist in the cell lysing step of the assay. In some arrangements, the lysing agent comprises a formulation, including, but not limited to the following three formulations:

Lysis Formula #1:
   10 mM Tris
   0.25% Igepal CA-630
   150 mM NaCl

Lysis Formula #2:
   10 mM Tris-HCl
   10 mM NaCl
   10 mM EDTA
   0.5% Triton-X100

Lysis Formula #3:
   0.1 M LiCl
   0.1 M Tris-HCl
   1% SDS
   10 mm EDTA

The next chamber is the liquid reagent mixing chamber. Once the sample has been sonicated and cell lysis has occurred, the freed nucleic acid is then pushed to the liquid reagent mixing chamber via pressure from the plunger column. The liquid reagent chamber contains the liquid-stable components of the rRT-PCR reagent mixture. Example components held in this chamber are, in some arrangements: Tris, IX LCGreen Dye, free nucleotides, $MgCl_2$ or sulforhodamine B.

The next chamber is the lyophilized reagent mixing chamber. This chamber contains a freeze-dried or lyophilized form of reagents that are not able to be stored for long periods in a liquid or hydrated state such as proteins.

Example components that would be lyophilized for long-term storage in the assay device are, in some arrangements: primers, polymerases, reverse transcriptase or bovine serum albumin (BSA).

The next chamber is the PCR chamber, this chamber is located external to the main section of the pod in the PCR fin. This chamber is where the final mixed PCR solution (containing the freed nucleic acid from the initial sample and all of the PCR reagents) is sent prior to the rRT-PCR process.

The final chamber is the waste chamber. This chamber holds all the discarded components throughout the cycles of the assay device. For example, when the wash solution is pushed through the sonication chamber, the solution is sent directly to the waste chamber upon exiting the sonication chamber. The volume of this chamber should be at minimum the total volume of all the liquid in the pod, plus the volume of the sample added.

PCR Methods

The method of some arrangements performs rRT-PCR for rapid detection and confirmation of the presence of SARS-CoV-2 in a sample. In order to control the heating and cooling process necessary for a RT-PCR reaction to occur, the system of some arrangements uses the heating apparatus 17 as a thermal cycler with dual heating elements that provide the necessary temperature cycles.

The discs 65, 66 of the heating apparatus 17 rotate rapidly during the extreme rRT-PCR cycling to apply different heat levels to heat the PCR chamber to the desired temperatures. Heating elements 69a, 69b are located on opposite sides of the disc and each occupy an area of a quarter of the surface area of the disc. Each heating element 69a, 69b is programmed to reach a certain temperature.

The first heating element 69a heats initially to 45° C., pauses for the reverse transcriptase step, then heats to its PCR temperature of 55° C. The second heating element 69b heats to 95° C. and is only used during the PCR step. The other two sections of the disc 65 serve as insulating areas between the heating elements 69a, 69b.

In some arrangement, the heat cycling occurs as follows: a ramp up to 45° C. of the first heating element 69a while the PCR chamber is exposed to an insulating section of the disc. Once the first heating element reaches 45° C., the disc 65 rotates to expose the PCR chamber to the second heating element 69b for 2 seconds to allow the reverse transcriptase process to occur. Immediately following that, the first heating element heats to 55° C. and the PCR process begins.

In some arrangements, the disc 65 begins to rapidly alternate between exposing the PCR chamber to the first and second heating elements for approximately 30-35 cycles of heating and cooling. After each rotation of the disc 65, the temperature of the liquid in the PCR chamber is monitored using passive fluorescence detection of the sulforhodamine B dye.

When the second heating element 69b is adjacent to the PCR chamber and the temperature of the liquid within the PCR chamber reaches 95° C., the disc 65 is triggered to rotate and move first heating element 69a adjacent to the PCR chamber. When the temperature then drops to 55° C., the disc 65 rotates back to the second heating element 69b. This completes one cycle.

Following the last PCR cycle, the first heating element 69a is rotated adjacent to the PCR chamber and begins heating at a rate of 8° C./s to a temperature between 90° C. and 100° C. to allow for the melting analysis to be performed to confirm the presence of specific PCR products.

Infectious Disease Screening Device

An infectious disease screening device 100 of some arrangements comprises eight main components: a chamber array containing various liquid chambers and passages, a sonication chamber, valves, pressure inlets (e.g. for attaching a Luer lock syringe), particulate filters, a PCR printed circuit board with heating elements and microfluidic chambers, PCR reagents and a final detection chamber.

Figure 25:
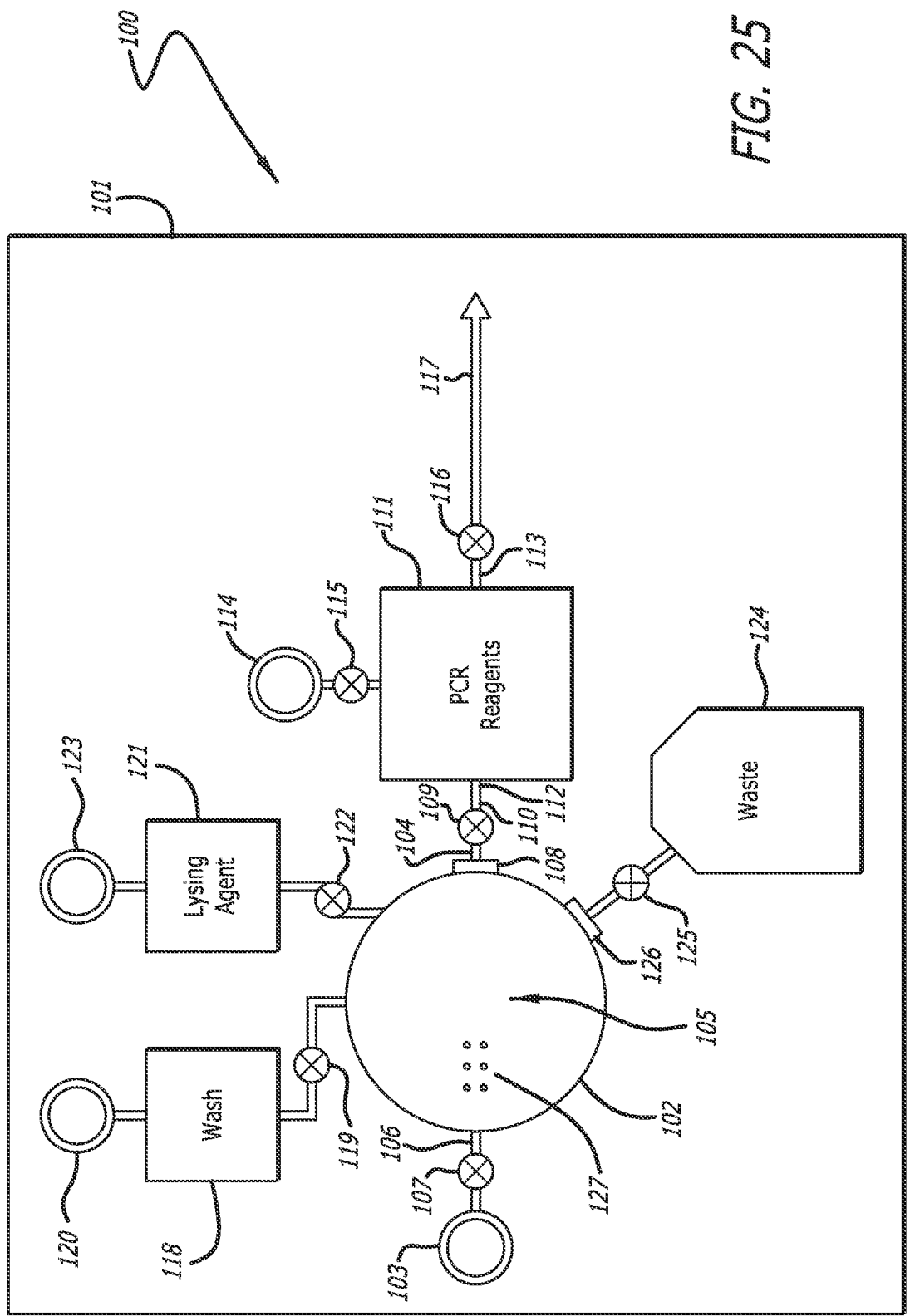
FIG. 25 is a schematic diagram of a chamber array of an assay device of some arrangements.

Whilst the arrangements described above comprise an assay device 2 having a transfer arrangement in the form of a piston, an infectious disease screening device 100 of other arrangements comprises chambers formed on a substrate 101, as shown in FIG. 25. In some arrangements, the substrate 101 is entirely or at least partly composed of silicon. The components of the infectious disease screening device 100 are formed in or on a film deposited on the silicon substrate and/or by etching in the silicon substrate. In some arrangements, the infectious disease screening device 100 is at least partly formed from a silicon wafer which is processed using techniques that are more traditionally used for manufacturing semiconductor microchips.

The use of the substrate enables the infectious disease screening device to be manufactured at low cost and in a high volume because existing semiconductor processing techniques allow for such low cost and high volume production.

The infectious disease screening device 100 comprises a sonication chamber 102 formed on the substrate 101. The sonication chamber 102 has a sample inlet 103, a sample outlet 104 and an ultrasonic transducer 105.

The sample inlet 103 is coupled in fluid communication with the sonication chamber 102 by a flow path 106. A valve 107 is provided along the flow path 106 to selectively allow or prevent a sample liquid from flowing from the sample inlet 103 into the sonication chamber 102.

The sample outlet 104 is provided with a filter 108 which filters sample fluid flowing out from the sample outlet 104. A valve 109 is provided along a fluid flow path 110 which is coupled in fluid communication with the sample outlet 104.

The ultrasonic transducer 105 is configured to generate ultrasonic waves to lyse cells in a sample fluid within the sonication chamber 102. The ultrasonic transducer 105 is configured to be controlled to oscillate to generate ultrasonic waves by a controller, such as the controller 23 described above. The infectious disease screening device 100 of some arrangements comprises the controller 23 described above. The controller 23 is coupled electrically to the ultrasonic transducer 105 to control the ultrasonic transducer 105 to generate ultrasonic waves.

The infectious disease screening device 100 comprises a reagent chamber 111 which is formed on the substrate 101 for receiving a liquid PCR reagent. The reagent chamber 111 has an inlet 112 and an outlet 113. The inlet 112 is coupled with the sample outlet 104 of the sonication chamber 102. The reagent chamber 111 is provided with a pressure drive port 114 which is in fluid communication with the PCR chamber 111, with a valve 115 being provided between the pressure drive port 114 and the reagent chamber 111.

The pressure drive port 114, and the other pressure drive ports described herein, are configured to be connected to a pressure drive arrangement. The pressure drive arrangement may be any kind of pressure drive arrangement. In some arrangements, the pressure drive arrangement is a Luer lock syringe. In other arrangements, the pressure drive arrangement is a pressure drive arrangement within the system 1 which is controlled by the controller 23. As will be described in more detail below, the pressure drive arrangement applies a positive or negative pressure to a pressure drive port which acts on fluid within one or more chambers of the infectious disease screening device 100 to cause the fluid to flow between the chambers.

The outlet 113 of the reagent chamber 111 is coupled via a valve 116 to an outlet flow path 117. As the fluid outlet 117 is coupled fluidly with a PCR chamber, as described below.

The infectious disease screening device 100 further comprises at least one further chamber which is formed on the substrate 101. One such further chamber is a wash chamber 118 which is coupled fluidly via a valve 119 to the sonication chamber 102. A pressure drive port 120 is provided on the wash chamber 118 such that a pressure drive arrangement can exert a pressure to drive a wash liquid from within the wash chamber 118 into the sonication chamber 102.

In some arrangements, the infectious disease screening device 100 further comprises a lysing agent chamber 121 which is coupled fluidly with the sonication chamber 102 via a valve 122. The lysing agent chamber 121 is provided with a pressure drive port 123 which is configured to apply a pressure to drive a lysing agent liquid from the lysing agent chamber 121 into the sonication chamber 102.

The infectious disease screening device 100 of some arrangements further comprises a waste chamber 124 which is coupled fluidly with the sonication chamber 102 via a valve 125 and a filter 126. In other arrangements, the number of chambers within the infectious disease screening device 100 may be different from the arrangement described above. In some arrangements, the number of chambers can vary from one chamber to as many as ten chambers. For the SARS-CoV-2 infectious disease screening device, the infectious disease screening device comprises six chambers.

In use, a user injects a sample that is to be analyzed into the sample inlet 103. The sample is preferably placed into an elution buffer prior to being added to the infectious disease screening device 100.

In some arrangements, the elution buffer consists of: 1 M Imidazole solution, 1 M Tris, 0.5 M EDTA, Milli-Q, sterile saline or Deionized water.

Figure 26:
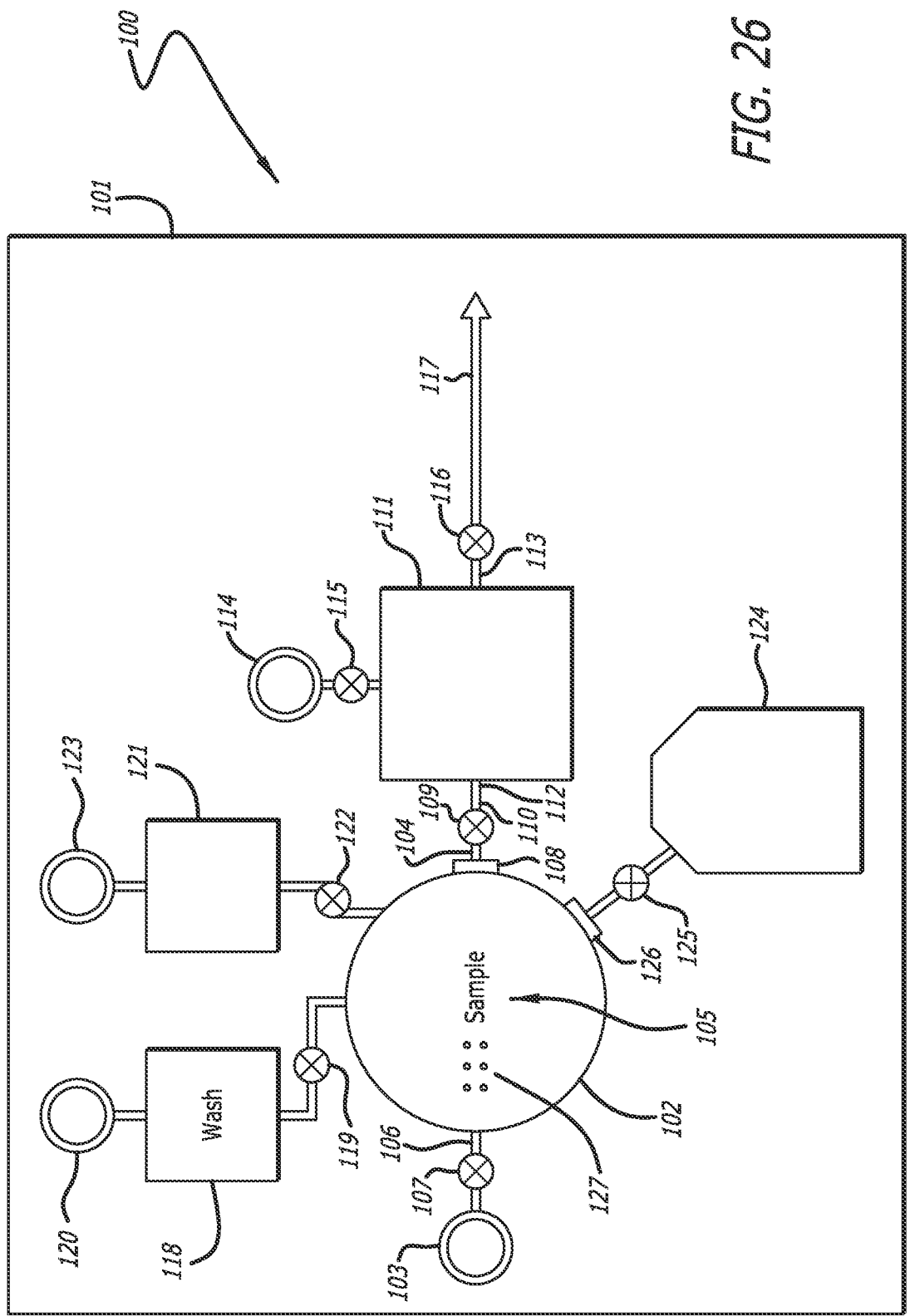
FIG. 26 is a schematic diagram of a chamber array of an assay device of some arrangements.

When the target sample is loaded into the device via the sample inlet 103, the sample is deposited directly into the sonication chamber 102, as shown in FIG. 26. In some arrangements, the sonication chamber 102 has a volume of 100 µl to 1000 µl. In some arrangements, the sonication chamber 102 comprises ports to all of the other chambers in the infectious disease screening device 100. The flow of liquid through these ports is directed by a system of valves that can be opened or closed by the user and/or by the controller 23.

The ports that lead from the sonication chamber 102 to the waste chamber 124 and the PCR reagent chamber 111 include filters 126, 108. In some arrangements, the filters 126, 108 have pores of 0.1 µm to 0.5 µm in diameter. The filters trap the target cells and/or viral particles and retain them in the sonication chamber 102 as various washes and other solutions pass through the sonication chamber 102 and into the waste chamber 124. The filter 108 on the PCR reagent port 104 serves to contain the cells and/or viral particles within the sonication chamber 102 until lysis occurs. After lysis, the pores in the filter 108 are designed to be large enough to still trap the broken cells and/or viral particles, but allow their genetic material to pass through.

In some arrangements, the base of the sonication chamber 102 is a piezoelectric disc which functions as the ultrasonic transducer 105 to send acoustic waves through the liquid medium of the filled sonic chamber to disrupt the target cells and release their genetic material. In some arrangements, the height of the sonication chamber 102 is approximately 200 µm.

In some arrangements, the sonication chamber 102 contains beads 127 or microbeads with a diameter of approximately 100 µm (only some of which are shown in FIG. 25). In some arrangements, approximately half of the beads 127 are buoyant so they exist near the top of the sonication chamber 102 during sonication and the other half are designed to not be buoyant and exist near the bottom of the sonication chamber 102. Between the two types of beads 127, a majority of the "lysing area" within the sonication chamber 102 will be encompassed with beads 127 that can help disrupt cell membranes during sonication.

The next chamber is the wash chamber 118. In use, the wash chamber 118 contains an excess amount (3 ml to 5 ml) of an elution buffer as mentioned above. The wash buffer is used to wash the sample once it is delivered to the sonication chamber 102 and remove any potential contaminants.

Figure 27:
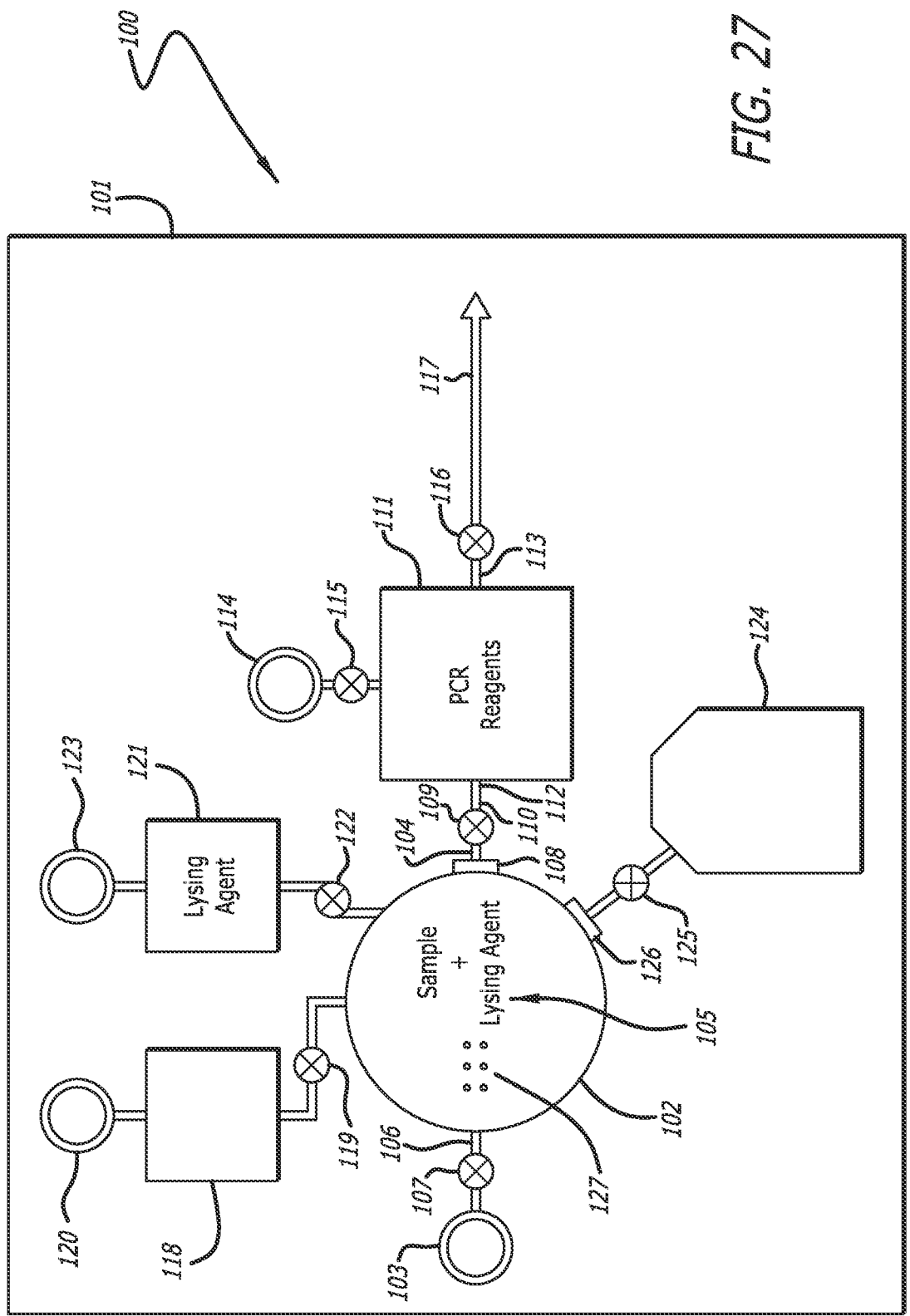
FIG. 27 is a schematic diagram of a chamber array of an assay device of some arrangements.
Figure 28:
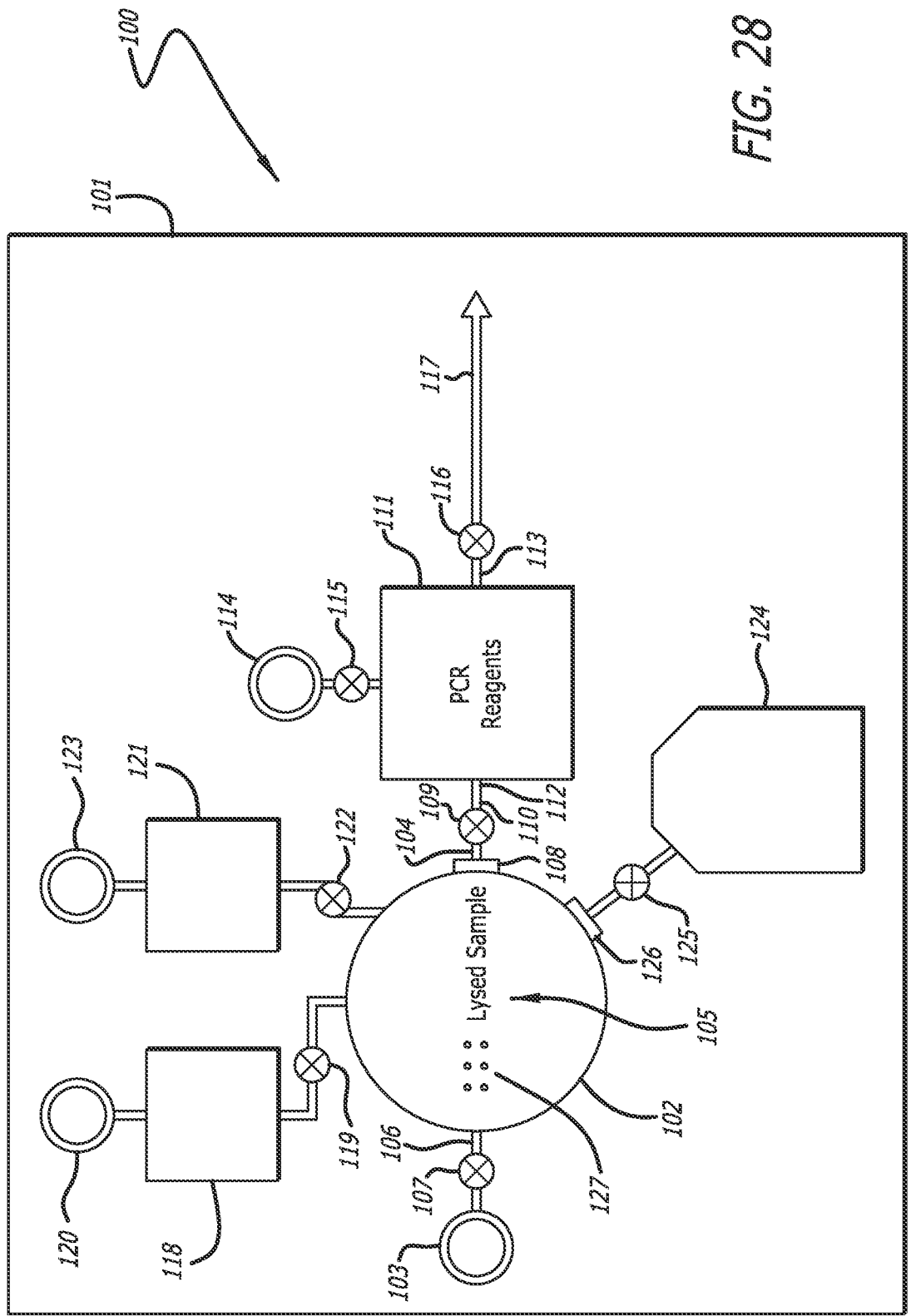
FIG. 28 is a schematic diagram of a chamber array of an assay device of some arrangements.
Figure 29:
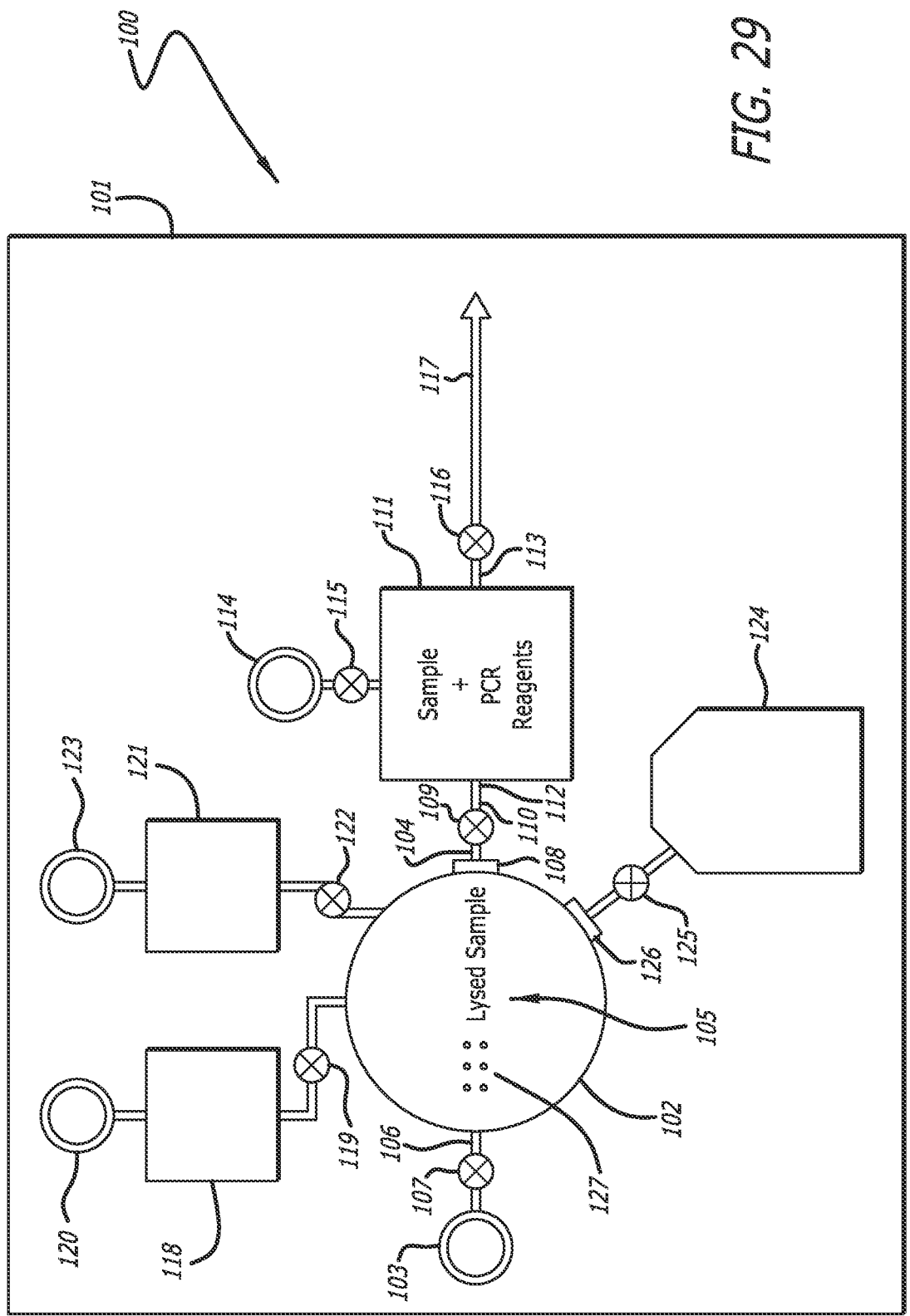
FIG. 29 is a schematic diagram of a chamber array of an assay device of some arrangements.
Figure 30:
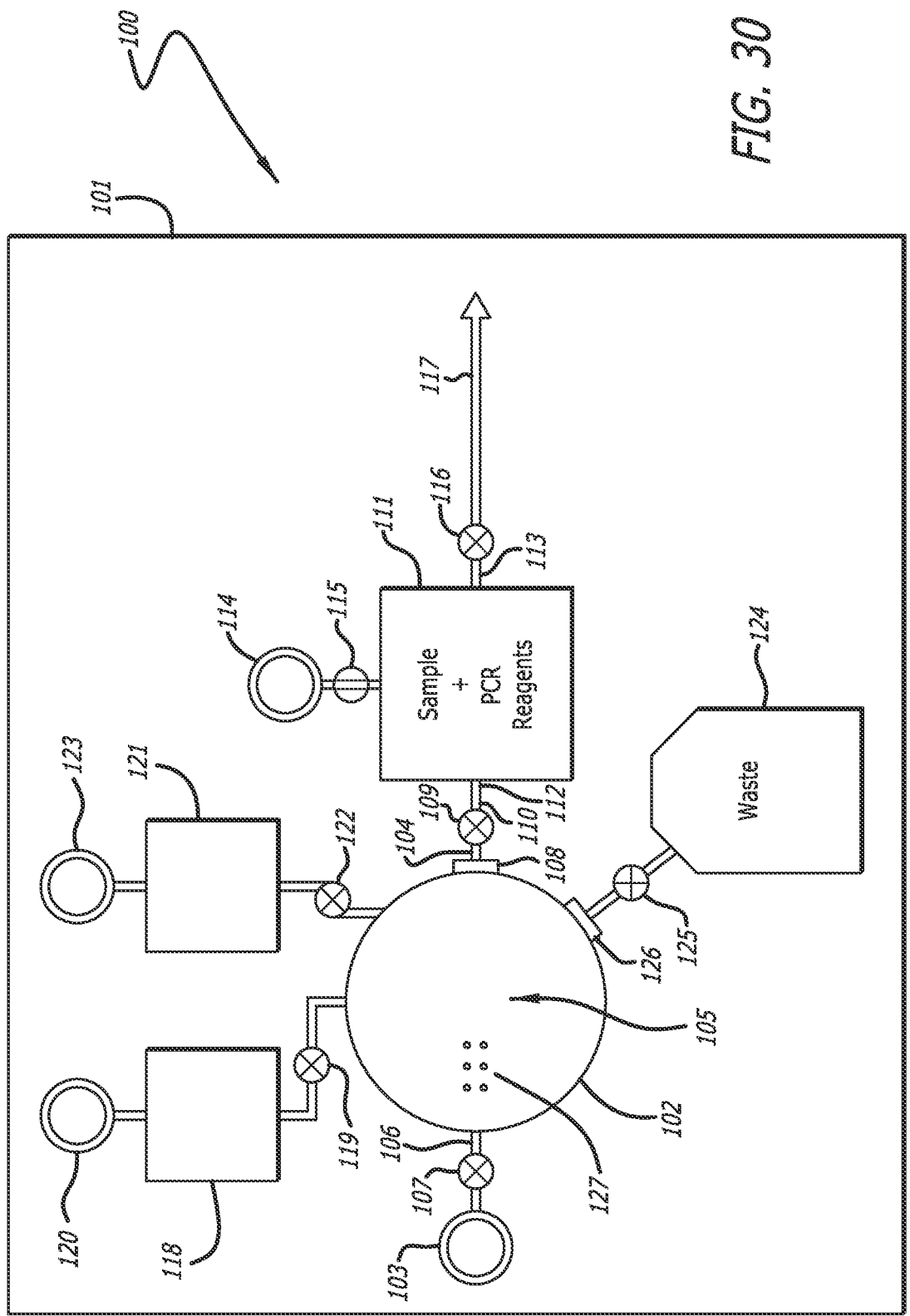
FIG. 30 is a schematic diagram of a chamber array of an assay device of some arrangements.

The next chamber is the lysing agent chamber 121, The lysing agent chamber 121 contains a mixture of chemicals to assist in the cell lysing step of the assay. A lysing agent is pushed from the lysing agent chamber 121 into the sonication chamber 102 where it mixes with the sample, as shown in FIG. 27. In some arrangements, lysing agent consists of formulations, including, but not limited to:

Lysis Formula #1:
  10 mM Tris
  0.25% Igepal CA-630
  150 mM NaCl
Lysis Formula #2:
  10 mM Tris-HCl
  10 mM NaCl
  10 mM EDTA
  0.5% Triton-X100
Lysis Formula #3:
  0.1 M LiCl
  0.1 M Tris-HCl
  1% SDS
  10 mm EDTA The next chamber is the PCR reagent chamber 111. Once the sample has been sonicated and cell lysis has occurred, as shown in FIG. 28, the freed nucleic acid is then pushed through the filter 108 to the PCR reagent chamber 111, as shown in FIG. 29. The PCR reagent chamber 111 contains the components needed for the rRT-PCR process. The sample enters the PCR reagent chamber 111 and is then toggled in and out of the PCR reagent chamber 111 by pressure exerted by a pressure drive arrangement (not shown) coupled to the pressure drive port 114. This toggling back and forth ensures the sample is sufficiently mixed with the PCR reagents, as shown in FIG. 30. Once the sample and PCR reagents are sufficiently mixed, the mixture is then pushed from the PCR reagent chamber 111 out through the flow path 117 to a PCR chamber. The PCR chamber is, in some arrangements, a channel in a PCR heating arrangement where the RT-PCR process will occur, as described below.

The final chamber is the waste chamber 124. The waste chamber 124 holds all the discarded components throughout the cycles of the chamber array. For example, when the wash solution is pushed through the sonication chamber 102, the solution is sent directly to the waste chamber 124 upon exiting the sonication chamber 102. The minimum volume of the waste chamber 124 is the total volume of all the liquid in the infectious disease screening device 100, plus the volume of the sample added.

PCR Reagents

In some arrangements, the PCR reagents in the PCR reagent chamber 111 are selected to facilitate the extreme rRT-PCR process as well as to allow for temperature monitoring via fluorescence.

In some arrangements, the PCR reagent formula is as follows: 5 µM of each forward and reverse primer (6 total primers, 2 sets for detecting SARS-CoV-2 and 1 set to serve as a control for a successful PCR reaction), IX LCGreen+ dye, 0.2 µM of each deoxynucleoside triphosphate (dNTP): dATP, dTTP, dGTP, dCTP, 50 mM Tris, 1.65 µM KlenTaq, 25 ng/µL BSA, 1.25 U/µL Malone Murine leukemia virus reverse transcriptase (MMLV), and 7.4 mM $MgCl_2$.

PCR Methods

Some examples of rRT-PCR processes are the processes described in international patent application no. PCT/US2016/060650 for rapid detection and confirmation of the presence of SARS-CoV-2 in a sample, incorporated by reference herein.

Figure 31:
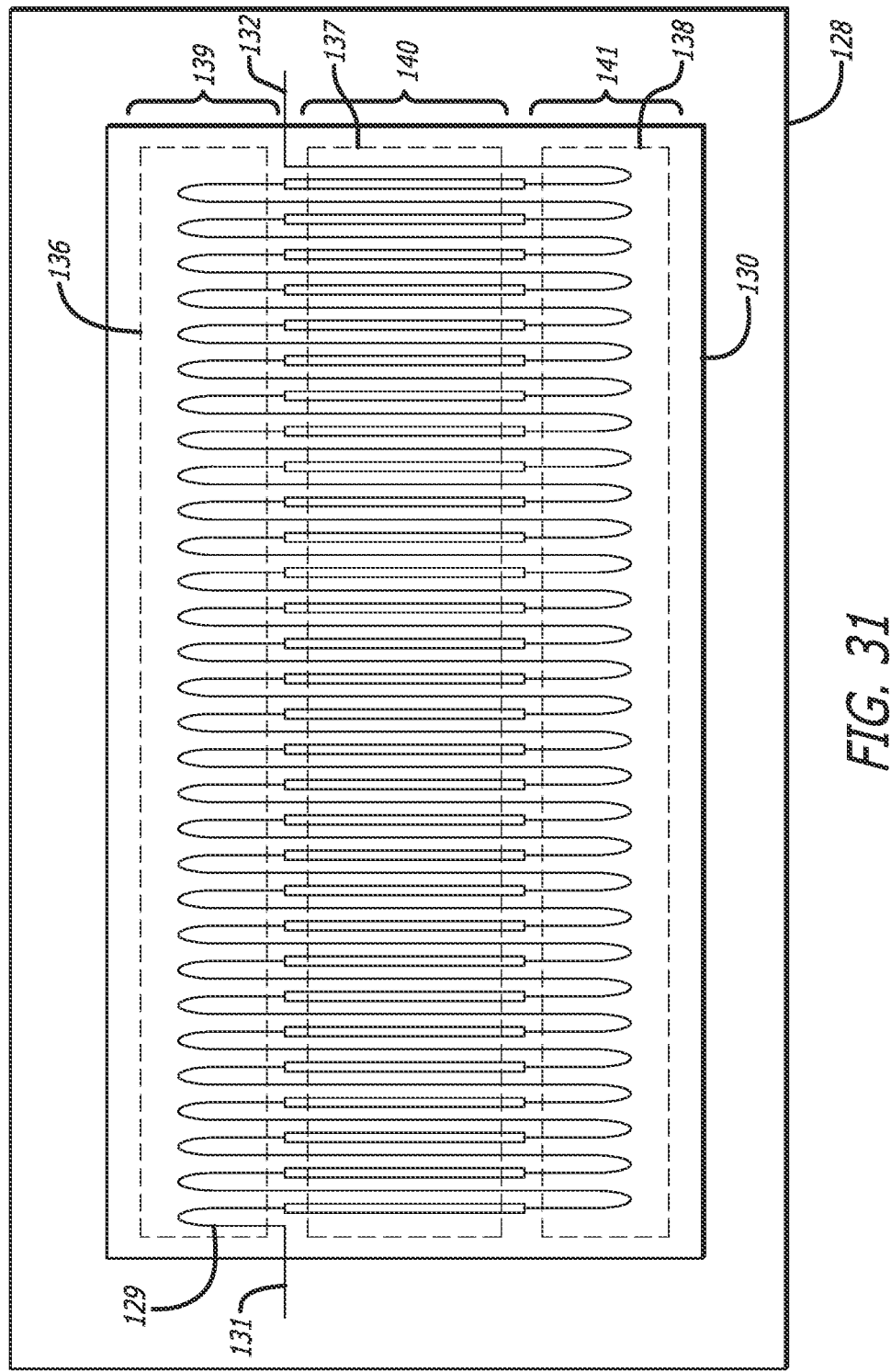
FIG. 31 is a schematic top view of a PCR heating arrangement of an assay device of some arrangements.

In order to control the heating and cooling process necessary for a RT-PCR reaction to occur, the sample is output from the PCR reagent chamber 111 to a heating arrangement 128, as shown in FIG. 31. The heating arrangement 128 comprises a channel 129 which is formed on a substrate 130. The channel 129 defines a fluid flow path between a channel inlet 131 and a channel outlet 132. The channel functions as a PCR chamber for performing a PCR process on a sample fluid flowing along the channel 129.

In some arrangements, the substrate 130 comprising the chamber array described above is formed integrally with the substrate 101 of the heating arrangement 128. In some embodiments, the substrates 130, 101 are portions of the same silicon wafer.

In some arrangements, the heating arrangement 128 is a microfluidic chip containing microchannels of varying sizes and heating elements to heat and cool the sample as it flows through the channels.

Figure 32:
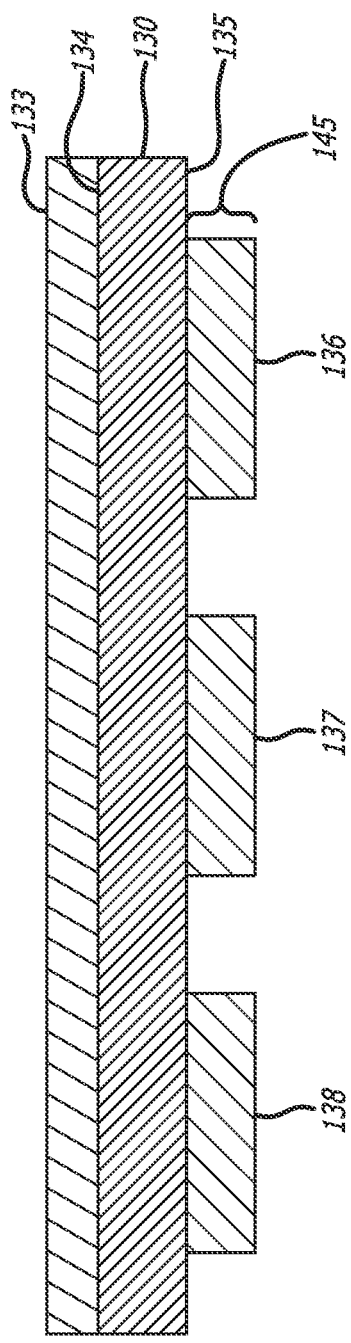
FIG. 32 is a schematic side view of the PCR heating arrangement shown in FIG. 31.

In some arrangements, the channel 129 is formed in a polyimide layer 133 which is deposited on the substrate 130, shown in FIG. 32. The polyimide layer 133 is deposited on a first side 134 of the substrate 130.

A second side 135 of the substrate 130 carries a first heating element 136. In this arrangement, the heating arrangement 128 comprises a second heating element 137 and a third heating element 138. The heating elements 136-138 are positioned adjacent one another on the second side 135 of the substrate 130. In some arrangements, the heating elements 136-138 are of copper which is deposited on the substrate 130 using printed circuit board manufacturing techniques. In some arrangements, the copper has a conductivity of approximately 1.7 E−8 Ω·m. The heating elements 136-138 each have a predetermined electrical resistance which causes the temperature of the heating elements 136-138 to increase when a current flows through the heating elements 136-138. In some arrangements, each heating element 136-138 has a resistance of approximately 2.5Ω.

In some arrangements, an electrical connection is established (directly or indirectly) between the heating elements 136-138 and the controller 23. The controller 23 controls the supply of electricity to each of the heating elements 136-138 which in turn controls the temperature of each of the heating elements 136-138.

Figure 33:
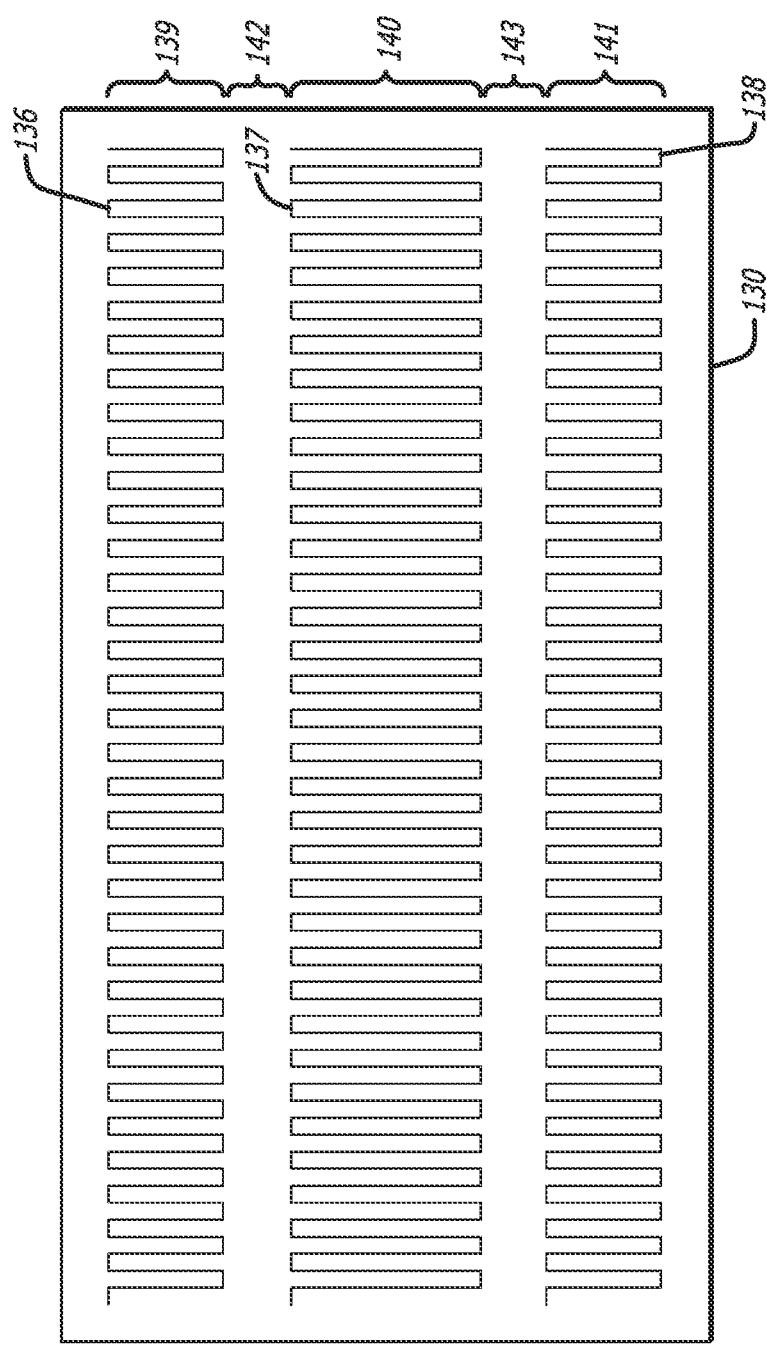
FIG. 33 is a schematic top view of heating elements of the PCR heating arrangement shown in FIG. 31.

Referring now to FIGS. 33-35, each of the heating elements 136-138 is formed along the length of the substrate 130. Each heating element 136-138 comprises multiple interconnected S-shaped turns. The first heating element 136 has an overall first width 139, the second heating element 137 has an overall second width 140 and the third heating element 138 has an overall third width 141. In this arrangement, the first and third overall widths 139, 141 are approximately 6 mm and the second overall width 140 is approximately 11.5 mm. The spacings 142, 143 between the heating elements 136-138 are approximately 0.5 mm.

Each of the heating elements 136-138 is an elongate electrical conductor which, in this arrangement, has a conductor width 144 of approximately 100 µm and a conductor depth 145 of approximately 18 µm. Each of the heating elements 136-138 has a turn width 146 of approximately 400 µm.

As will be described in more detail below, the first heating element 136 is configured to heat to a temperature of approximately 95° C., the second heating element 137 is configured to heat to a temperature of approximately 77° C. and the third heating element 138 is configured to heat to a temperature of approximately 55° C.

Figure 36:
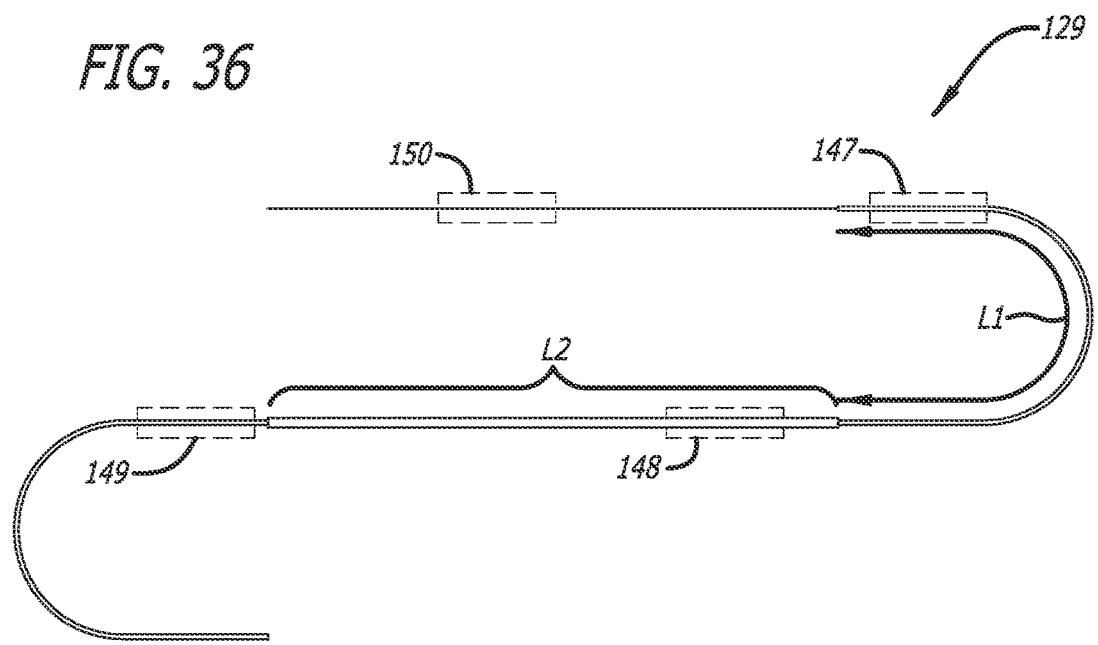
FIG. 36 is a schematic view of part of a channel of the PCR heating arrangement shown in FIG. 31.

Returning now to FIG. 31, the channel 129 is formed from multiple interconnected S-shaped turns which provide a fluid flow path back and forth across the surface of the substrate 130. In this arrangement, there are thirty turns of the channel 129. The microfluidic channel is photopatterned into the polyimide film 133 with great accuracy. FIG. 36 shows one of the S-shaped turns of the channel 129.

Figure 37:
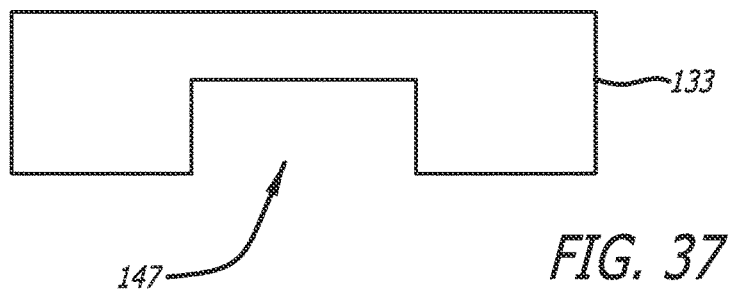
FIG. 37 is a schematic view of part of a channel of the PCR heating arrangement shown in FIG. 31.
Figure 38:
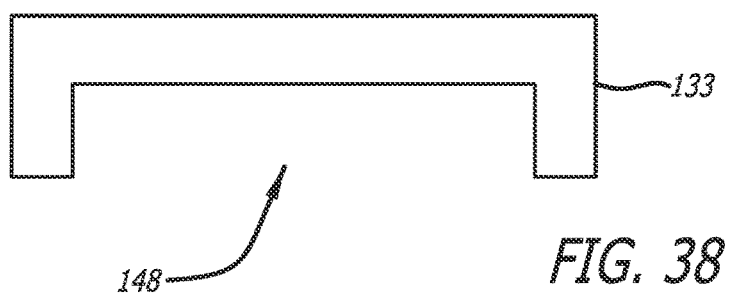
FIG. 38 is a schematic view of part of a channel of the PCR heating arrangement shown in FIG. 31.
Figure 39:
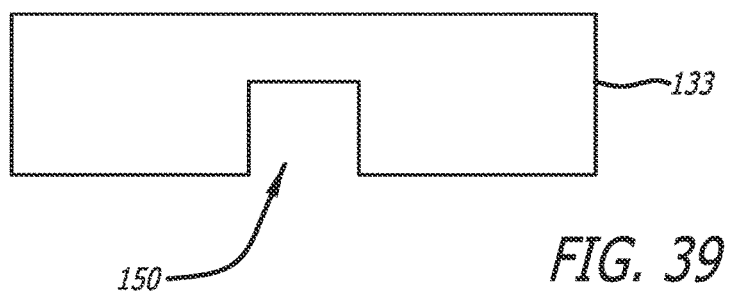
FIG. 39 is a schematic view of part of a channel of the PCR heating arrangement shown in FIG. 31.

Referring now to FIGS. 37-39, the channel 129 comprises a first channel portion 147 having a first cross-sectional area and a second channel portion 148 having a second cross-sectional area, wherein the second cross-sectional area is greater than the first cross-sectional area. In this arrangement, the first channel portion 147 has a depth of approximately 60 µm and a width of approximately 200 µm and the second channel portion 148 has a depth of approximately 60 µm and a width of approximately 400 µm.

In this arrangement, the channel 129 comprises a third channel portion 149 having a third cross-sectional area which is the same as the first cross-sectional area.

In this arrangement, the channel 129 comprises a fourth channel portion 150 having a third cross-sectional area which is less than the first and second cross-sectional areas. In this arrangement, the fourth channel portion 150 has a depth of approximately 60 µm and a width of approximately 100 µm.

In this arrangement, the first and third channel portions 147, 149 each have a length L1 of approximately 12.5 mm and the second channel portion 148 has a length L2 of approximately 12.5 mm.

The sample is pushed from the PCR reagent chamber 111, through the channel inlet 131 and along the channel 129 of the heating arrangement 128 of the PCR arrangement. In some arrangements, the inlet velocity of the sample is approximately 5 mm/s.

In this arrangement, each turn of the channel 129 comprises four distinct 12.5 mm long sections of different widths in order to control the rate of flow through each section. The first section of each wind is 200 µm wide. Each wind of the microfluidic channel traverses the substrate 130 from one side to the other and each wind passes over the three heating elements 136-138.

The first portion 147 of the wind passes over the first heating element 136 set to 95° C. The second portion 148 of the wind passes over the second heating element 137 set to 77° C. The third and "final" portion 149 of the wind is identical but opposite to the first portion 147; it is 200 μm wide but it passes over the third heating element 138 which is set to 55° C.

The fourth portion 150 of the wind is a small 100 μm section that connects the third portion 149 of the wind back to the first portion 147 of the next wind. The fourth portion 150 is small so that the liquid flowing through it moves quickly back to the first portion 147 of the next wind and does not spend a significant length of time over the second heating element 137.

As the sample passes through the 30 heating and cooling loops, the rRT-PCR reaction occurs and by the time the sample exits at the channel outlet 132, it has completed the 30 cycles of heating and cooling required for completion of the rRT-PCR process. The sample exits the heating arrangement 128 and flows into a detection chamber. In some arrangements, the detection chamber is a chamber of the detection arrangement 70 of the system described herein.

The detection arrangement 70 detects fluorescence emitted from the sample and reports the result of the assay as described herein. In some arrangements, the detection arrangement is a SARS-CoV-2 virus detection apparatus which is coupled to the channel outlet 132. The detection apparatus detects a presence of the SARS-CoV-2 virus that causes COVID-19 disease in a sample fluid flowing out of the channel outlet. The detection apparatus provides an output which is indicative of whether or not the SARS-CoV-2 virus detection apparatus detects the presence of the COVID-19 disease in the sample fluid. In other arrangements, the detection apparatus detects the presence of a different infectious disease from COVID-19 disease.

In some arrangements, the formation of the sonication chamber (102), the reagent chamber (111), any further chambers, and the heating arrangement (128) on the same substrate (101) in combination with the controller 23 provides a compact and relatively low cost device (compared with larger laboratory PCR systems). Consequently, the device (100) of some arrangements can be mass produced easily using conventional semiconductor manufacturing techniques.

The device or system of some arrangements seeks to provide test results within 10 minutes and, in some arrangements, as little as 5 minutes or less. This is significantly faster than conventional PCR tests and it opens up the possibility for rapid testing at homes, shops, entertainment venues, as well as airports, bus and train terminals and other transport facilities.

The device or system of some arrangements is highly portable and can be carried easily to a location where testing is required. The efficient operation of the device or system enables the device or system of some arrangements to be powered by a battery, enabling the system to provide tests at virtually any location.

The devices and systems of the arrangements that can screen a saliva or sputum sample make the screening process easier and quicker, especially for children or sensitive individuals, as compared with systems that require a nasopharyngeal or oropharyngeal swab sample.

The foregoing outlines features of several embodiments so that those of ordinary skill in the art may better understand various aspects of the present disclosure. Those of ordinary skill in the art should appreciate that they may readily use the present disclosure as a basis for designing or modifying other processes and structures for carrying out the same purposes and/or achieving the same advantages of various embodiments introduced herein. Those of ordinary skill in the art should also realize that such equivalent constructions do not depart from the spirit and scope of the present disclosure, and that they may make various changes, substitutions, and alterations herein without departing from the spirit and scope of the present disclosure.

Although the subject matter has been described in language specific to structural features or methodological acts, it is to be understood that the subject matter of the appended claims is not necessarily limited to the specific features or acts described above. Rather, the specific features and acts described above are disclosed as example forms of implementing at least some of the claims.

Various operations of embodiments are provided herein. The order in which some or all of the operations are described should not be construed to imply that these operations are necessarily order dependent. Alternative ordering will be appreciated having the benefit of this description. Further, it will be understood that not all operations are necessarily present in each embodiment provided herein. Also, it will be understood that not all operations are necessary in some embodiments.

Moreover, "exemplary" is used herein to mean serving as an example, instance, illustration, etc., and not necessarily as advantageous. As used in this application, "or" is intended to mean an inclusive "or" rather than an exclusive "or". In addition, "a" and "an" as used in this application and the appended claims are generally be construed to mean "one or more" unless specified otherwise or clear from context to be directed to a singular form. Also, at least one of A and B and/or the like generally means A or B or both A and B. Furthermore, to the extent that "includes", "having", "has", "with", or variants thereof are used, such terms are intended to be inclusive in a manner similar to the term "comprising". Also, unless specified otherwise, "first," "second," or the like are not intended to imply a temporal aspect, a spatial aspect, an ordering, etc. Rather, such terms are merely used as identifiers, names, etc. for features, elements, items, etc. For example, a first element and a second element generally correspond to element A and element B or two different or two identical elements or the same element.

Also, although the disclosure has been shown and described with respect to one or more implementations, equivalent alterations and modifications will occur to others of ordinary skill in the art based upon a reading and understanding of this specification and the annexed drawings. The disclosure comprises all such modifications and alterations and is limited only by the scope of the following claims. In particular regard to the various functions performed by the above described features (e.g., elements, resources, etc.), the terms used to describe such features are intended to correspond, unless otherwise indicated, to any features which performs the specified function of the described features (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

Embodiments of the subject matter and the functional operations described herein can be implemented in digital electronic circuitry, or in computer software, firmware, or hardware, including the structures disclosed in this specification and their structural equivalents, or in combinations of one or more of them.

Features of some embodiments are implemented using one or more modules of computer program instructions encoded on a computer-readable medium for execution by, or to control the operation of, a data processing apparatus or a controller. The computer-readable medium can be a manufactured product, such as hard drive in a computer system or an embedded system. The computer-readable medium can be acquired separately and later encoded with the one or more modules of computer program instructions, such as by delivery of the one or more modules of computer program instructions over a wired or wireless network. The computer-readable medium can be a machine-readable storage device, a machine-readable storage substrate, a memory device, or a combination of one or more of them.

The terms "computing device" and "data processing apparatus" encompass all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, a runtime environment, or a combination of one or more of them. In addition, the apparatus can employ various different computing model infrastructures, such as web services, distributed computing and grid computing infrastructures.

The processes and logic flows described in this specification can be performed by one or more programmable processors executing one or more computer programs to perform functions by operating on input data and generating output.

As used herein, in some embodiments the term module comprises a memory and/or a processor configured to control at least one process of a system or a circuit structure. The memory storing executable instructions which, when executed by the processor, cause the processor to provide an output to perform the at least one process. Embodiments of the memory include non-transitory computer readable media.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Devices suitable for storing computer program instructions and data include all forms of non-volatile memory, media and memory devices, including by way of example semiconductor memory devices, e.g., EPROM (Erasable Programmable Read-Only Memory), EEPROM (Electrically Erasable Programmable Read-Only Memory), and flash memory devices; magnetic disks, e.g., internal hard disks or removable disks; magneto-optical disks; and CD-ROM and DVD-ROM disks.

To provide for interaction with a user, some embodiments are implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

In the present specification "comprise" means "includes or consists of" and "comprising" means "including or consisting of".

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features; be utilized for realizing the invention in diverse forms thereof.

What is claimed is:

1. An infectious disease screening device for rapid detection of an infectious agent present in a sample fluid, the screening device comprising:
   a substrate which is at least partly composed of silicon, the substrate comprising a sonication chamber having a sample inlet and a sample outlet;
   an ultrasonic transducer in ultrasonic communication with the sonication chamber, wherein the ultrasonic transducer generates ultrasonic waves in a frequency range of approximately 2800 kHz to approximately 3200 kHz to lyse cells in the sample fluid within the sonication chamber;
   a controller comprising:
      an AC driver which generates an AC drive signal at a frequency within the frequency range of approximately 2800 kHz to approximately 3200 kHz and outputs the AC drive signal to drive the ultrasonic transducer;
   an extreme rRT-PCR cycler comprising:
      a channel defining a fluid flow path between a channel inlet and a channel outlet, the channel inlet being coupled with the outlet of the reagent chamber to receive at least part of the sample fluid flowing into the channel from the reagent chamber, wherein the channel is formed from a plurality of interconnected turns which provide a plurality of channel sections across the surface of the substrate, wherein each channel section of the plurality of channel sections comprises a first channel portion, a second channel portion and a third channel portion;
      a first heating element proximate each first channel portion;
      a second heating element proximate each second channel portion; and
      a third heating element proximate each third channel portion, wherein the controller controls:
         the first heating element to heat the sample fluid flowing along each first channel portion,
         the second heating element to heat the sample fluid flowing along each second channel portion, and
         the third heating element to heat the sample fluid flowing along each third channel portion to perform extreme rRT-PCR on the sample fluid;
      wherein the device further comprises:
         an infectious agent detection apparatus which is in communication with and coupled to the channel outlet, wherein the infectious agent detection apparatus detects a presence of an infectious agent that causes the infectious disease in the sample fluid flowing out of the channel outlet, wherein the infectious agent detection apparatus provides an output which is indicative of whether or not the detection apparatus detects the presence of the infectious agent in the sample fluid.

2. The infectious disease screening device of claim 1, wherein the active power monitor comprises:
a current sensor which senses a drive current of the AC drive signal driving the ultrasonic transducer, wherein the active power monitor provides the monitoring signal which is indicative of the sensed drive current.

3. The infectious disease screening device of claim 1, wherein the AC driver modulates the AC drive signal by pulse width modulation to maximize the active power being used by the ultrasonic transducer.

4. The infectious disease screening device of claim 1, wherein the device further comprises:
an active power monitor which monitors active power used by the ultrasonic transducer when the ultrasonic transducer is driven by the AC drive signal, wherein the active power monitor provides a monitoring signal which is indicative of the active power used by the ultrasonic transducer.

5. The infectious disease screening device of claim 4, wherein the device further comprises:
a memory storing executable instructions; and
a processor which receives the monitoring signal from the active power monitor, wherein the processor processes the executable instructions and controls the AC driver to drive the ultrasonic transducer at an optimum frequency at which a maximum active power is used by the ultrasonic transducer.

6. The infectious disease screening device of claim 5, wherein the memory stores instructions which, when executed by the processor, cause the processor to:
control the AC driver to alternately output the AC drive signal to the ultrasonic transducer at the optimum frequency for a first predetermined length of time and to not output the AC drive signal to the ultrasonic transducer for a second predetermined length of time.

7. The infectious disease screening device of claim 5, wherein the memory stores instructions which, when executed by the processor, cause the processor to:
alternately output the AC drive signal and to not output the AC drive signal according to an operating mode selected from:

| Operating mode | First predetermined length of time (seconds) | Second predetermined length of time (seconds) |
| --- | --- | --- |
| 1 | 4 | 2 |
| 2 | 3 | 2 |
| 3 | 2 | 2 |
| 4 | 1 | 2 |
| 5 | 1 | 1 |
| 6 | 2 | 1 |
| 7 | 3 | 1 |
| 8 | 4 | 1 |
| 9 | 4 | 3 |
| 10 | 3 | 3 |
| 11 | 2 | 3 |
| 12 | 1 | 3. |

8. The infectious disease screening device of claim 1, wherein the device further comprises:
a filter which is provided between the sonication chamber and the reagent chamber to filter the sample fluid flowing from the sonication chamber to the reagent chamber.

9. The infectious disease screening device of claim 8, wherein the filter has pores of 0.1 μm to 0.5 μm in diameter.

10. The infectious disease screening device of claim 1, wherein the substrate further comprises:
at least one further chamber, the at least one further chamber being coupled for fluid communication with the sonication chamber.

11. The infectious disease screening device of claim 10, wherein the device further comprises:
a plurality of valves which are controlled by the controller to selectively open and close to permit or restrict the flow of liquids between each further chamber and the sonication chamber.

12. The infectious disease screening device of claim 10, wherein the at least one further chamber stores a lysing agent having a formula selected from one of:
a first lysis formula consisting of 10 mM Tris, 0.25% Igepal CA-630 and 150 mM NaCl;
a second lysis formula consisting of 10 mM Tris-HCl, 10 mM NaCl, 10 mM EDTA and 0.5% Triton-X100; or
a third lysis formula consisting of 0.1 M LiCl, 0.1 M Tris-HCl, 1% SDS or 10 mm EDTA.

13. The infectious disease screening device of claim 1, wherein the sonication chamber has a volume of 100 μl to 1000 μl.

14. The infectious disease screening device of claim 1, wherein the sonication chamber contains a plurality of beads, each bead having a diameter of approximately 100 μm.

15. The infectious disease screening device of claim 1, wherein each first channel portion has a first cross-sectional area and each second channel portion has a second cross-sectional area, wherein the second cross-sectional area is greater than the first cross-sectional area.

16. The infectious disease screening device of claim 15, wherein:
each first channel portion has a depth of approximately 60 μm and a width of approximately 200 μm, and
each second channel portion has a depth of approximately 60 μm and a width of approximately 400 μm.

17. The infectious disease screening device of claim 15, wherein each third channel portion has a third cross-sectional area which the same as the first cross-sectional area.

18. The infectious disease screening device of claim 1, wherein the controller controls:
the first heating element to heat to a temperature of approximately 95° C.,
the second heating element to heat to a temperature of approximately 77° C., and
the third heating element to heat to a temperature of approximately 55° C.

19. The infectious disease screening device of claim 1, wherein the channel is formed from thirty interconnected turns.

20. The infectious disease screening device of claim 1, wherein the infectious agent detection apparatus detects a presence of an infectious agent that causes a disease selected from a group including influenza, coronavirus, measles, HIV, hepatitis, meningitis, tuberculosis, Epstein-Barr virus (glandular fever), yellow fever, malaria, norovirus, zika virus infection and anthrax.

* * * * *